(12) United States Patent
Burden et al.

(10) Patent No.: US 11,976,382 B2
(45) Date of Patent: May 7, 2024

(54) NUCLEIC ACID BASED BIOSENSOR AND METHODS THEREOF

(71) Applicant: Boise State University, Boise, ID (US)

(72) Inventors: Steven Burden, Boise, ID (US); Eric Hayden, Boise, ID (US); Nicholas Shults, Boise, ID (US)

(73) Assignee: Boise State University, Boise, ID (US)

( * ) Notice: Subject to any disclaimer, the term of this patent is extended or adjusted under 35 U.S.C. 154(b) by 462 days.

(21) Appl. No.: 16/949,217

(22) Filed: Oct. 20, 2020

(65) Prior Publication Data

US 2021/0123055 A1 Apr. 29, 2021

Related U.S. Application Data

(60) Provisional application No. 62/924,907, filed on Oct. 23, 2019.

(51) Int. Cl.
| | |
|---|---|
| *C40B 40/08* | (2006.01) |
| *C12N 15/10* | (2006.01) |
| *C12N 15/115* | (2010.01) |
| *G01N 21/64* | (2006.01) |

(52) U.S. Cl.
CPC .......... *C40B 40/08* (2013.01); *C12N 15/1048* (2013.01); *C12N 15/115* (2013.01); *G01N 21/6428* (2013.01); *C12N 2310/16* (2013.01); *C12N 2320/10* (2013.01); *C12N 2320/11* (2013.01); *C12N 2320/13* (2013.01); *G01N 2021/6439* (2013.01)

(58) Field of Classification Search
None
See application file for complete search history.

(56) References Cited

U.S. PATENT DOCUMENTS

| | | |
|---|---|---|
| 2012/0252699 A1 | 10/2012 | Jaffrey et al. |
| 2014/0220560 A1 | 8/2014 | Jaffrey et al. |
| 2016/0370355 A1 | 12/2016 | Krishnan et al. |

FOREIGN PATENT DOCUMENTS

WO        2018198013 A1    11/2018

*Primary Examiner* — Christian C Boesen
(74) *Attorney, Agent, or Firm* — McKee, Voorhees & Sease, PLC

(57) ABSTRACT

The present disclosure relates to oligonucleotide biosensors that bind to a fluorophore through a reporter domain and to one or more target ligand(s) through one or more target domain(s), which is connected to the reporter domain through one or more linker domain(s). The binding of the target ligand to the target domain affects the fluorescence of the fluorophore when excited by the appropriate wavelength of energy, either by causing dimming or allosteric fluorescence. Methods of selecting biosensors and their use to detect target ligands are also described.

32 Claims, 20 Drawing Sheets

Specification includes a Sequence Listing.

SEQUENCE LISTING

```
<160> NUMBER OF SEQ ID NOS: 23

<210> SEQ ID NO 1
<211> LENGTH: 25
<212> TYPE: RNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (3)..(3)
<223> OTHER INFORMATION: can be a, c, g, u; can be present or absent
<220> FEATURE:
<221> NAME/KEY: misc_feature
<222> LOCATION: (4)..(4)
<223> OTHER INFORMATION: can be a, c, g, u
<220> FEATURE:
<221> NAME/KEY: misc_feature
<222> LOCATION: (5)..(5)
<223> OTHER INFORMATION: can be present or absent
```

```
<220> FEATURE:
<221> NAME/KEY: misc_feature
<222> LOCATION: (6)..(6)
<223> OTHER INFORMATION: can be present or absent
<220> FEATURE:
<221> NAME/KEY: misc_feature
<222> LOCATION: (9)..(9)
<223> OTHER INFORMATION: can be a, c, g, u
<220> FEATURE:
<221> NAME/KEY: misc_feature
<222> LOCATION: (10)..(10)
<223> OTHER INFORMATION: can be a, c, g, u
<220> FEATURE:
<221> NAME/KEY: misc_feature
<222> LOCATION: (14)..(14)
<223> OTHER INFORMATION: can be a, c, g, u
<220> FEATURE:
<221> NAME/KEY: misc_feature
<222> LOCATION: (15)..(15)
<223> OTHER INFORMATION: can be a, c, g, u; can be present or absent
<220> FEATURE:
<221> NAME/KEY: misc_feature
<222> LOCATION: (16)..(16)
<223> OTHER INFORMATION: can be a, c, g, u; can be present or absent
<220> FEATURE:
<221> NAME/KEY: misc_feature
<222> LOCATION: (18)..(18)
<223> OTHER INFORMATION: can be a, c, g, u
<220> FEATURE:
<221> NAME/KEY: misc_feature
<222> LOCATION: (20)..(20)
<223> OTHER INFORMATION: can be a, c, g, u
<220> FEATURE:
<221> NAME/KEY: misc_feature
<222> LOCATION: (23)..(23)
<223> OTHER INFORMATION: can be a, c, g, u
<220> FEATURE:
<221> NAME/KEY: misc_feature
<222> LOCATION: (24)..(24)
<223> OTHER INFORMATION: can be a, c, g, u; can be present or absent
<220> FEATURE:
<221> NAME/KEY: misc_feature
<222> LOCATION: (25)..(25)
<223> OTHER INFORMATION: can be a, c, g, u

<400> SEQUENCE: 1
ggnngwggnn wggnnngngn hrnnn                                         25

<210> SEQ ID NO 2
<211> LENGTH: 39
<212> TYPE: RNA
<213> ORGANISM: Artificial Sequence
<220> FEATURE:
<223> OTHER INFORMATION: Aptamer

<400> SEQUENCE: 2
ggaucgcgga agggacggug cggagaggag acgcgaucc                          39

<210> SEQ ID NO 3
<211> LENGTH: 61
<212> TYPE: RNA
<213> ORGANISM: Artificial Sequence
<220> FEATURE:
<223> OTHER INFORMATION: Aptamer

<400> SEQUENCE: 3
ggaucgcgga agggaguacg ugcgaaagca cguacgaagg ugcggagagg agacgcgauc   60
c                                                                  61

<210> SEQ ID NO 4
<211> LENGTH: 62
<212> TYPE: RNA
```

```
<213> ORGANISM: Artificial Sequence
<220> FEATURE:
<223> OTHER INFORMATION: Aptamer

<400> SEQUENCE: 4
ggaucgcgga agggacggug aguacgugcg aaagcacgua cgaaggagag gagacgcgau    60
cc                                                                  62

<210> SEQ ID NO 5
<211> LENGTH: 62
<212> TYPE: RNA
<213> ORGANISM: Artificial Sequence
<220> FEATURE:
<223> OTHER INFORMATION: Aptamer

<400> SEQUENCE: 5
ggaucgcgga agggacggug cggagaguac gugcgaaagc acguacgaag gagacgcgau    60
cc                                                                  62

<210> SEQ ID NO 6
<211> LENGTH: 61
<212> TYPE: RNA
<213> ORGANISM: Artificial Sequence
<220> FEATURE:
<223> OTHER INFORMATION: Aptamer

<400> SEQUENCE: 6
ggaucgcgga aggugaguac gugcgaaagc acguacgaag gagaggagag ggacgcgauc    60
c                                                                   61

<210> SEQ ID NO 7
<211> LENGTH: 61
<212> TYPE: RNA
<213> ORGANISM: Artificial Sequence
<220> FEATURE:
<223> OTHER INFORMATION: Aptamer

<400> SEQUENCE: 7
ggaucgcgga aggugcggag aguacgugcg aaagcacgua cgaaggagag ggacgcgauc    60
c                                                                   61

<210> SEQ ID NO 8
<211> LENGTH: 62
<212> TYPE: RNA
<213> ORGANISM: Artificial Sequence
<220> FEATURE:
<223> OTHER INFORMATION: Aptamer

<400> SEQUENCE: 8
ggaucgcgga aggagaguac gugcgaaagc acguacgaag gagagggacg gugacgcgau    60
cc                                                                  62

<210> SEQ ID NO 9
<211> LENGTH: 34
<212> TYPE: RNA
<213> ORGANISM: Artificial Sequence
<220> FEATURE:
<223> OTHER INFORMATION: Aptamer

<400> SEQUENCE: 9
gcacguacga aggugcggag aggagacgcg aucc                                34
```

```
<210> SEQ ID NO 10
<211> LENGTH: 23
<212> TYPE: RNA
<213> ORGANISM: Artificial Sequence
<220> FEATURE:
<223> OTHER INFORMATION: Aptamer

<400> SEQUENCE: 10
ggaucgcgga agggaguacg ugc                                          23

<210> SEQ ID NO 11
<211> LENGTH: 24
<212> TYPE: RNA
<213> ORGANISM: Artificial Sequence
<220> FEATURE:
<223> OTHER INFORMATION: Aptamer

<400> SEQUENCE: 11
ggaucgcgga aggugaguac gugc                                         24

<210> SEQ ID NO 12
<211> LENGTH: 33
<212> TYPE: RNA
<213> ORGANISM: Artificial Sequence
<220> FEATURE:
<223> OTHER INFORMATION: Aptamer

<400> SEQUENCE: 12
gcacguacga aggagaggag agggacgcga ucc                               33

<210> SEQ ID NO 13
<211> LENGTH: 34
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (1)..(1)
<223> OTHER INFORMATION: can be a, c, g, u
<220> FEATURE:
<221> NAME/KEY: misc_feature
<222> LOCATION: (2)..(2)
<223> OTHER INFORMATION: can be a, c, g, u
<220> FEATURE:
<221> NAME/KEY: misc_feature
<222> LOCATION: (3)..(3)
<223> OTHER INFORMATION: can be a, c, g, u
<220> FEATURE:
<221> NAME/KEY: misc_feature
<222> LOCATION: (4)..(4)
<223> OTHER INFORMATION: can be a, c, g, u
<220> FEATURE:
<221> NAME/KEY: misc_feature
<222> LOCATION: (31)..(31)
<223> OTHER INFORMATION: can be a, c, g, u
<220> FEATURE:
<221> NAME/KEY: misc_feature
<222> LOCATION: (32)..(32)
<223> OTHER INFORMATION: can be a, c, g, u
<220> FEATURE:
<221> NAME/KEY: misc_feature
<222> LOCATION: (33)..(33)
<223> OTHER INFORMATION: can be a, c, g, u
<220> FEATURE:
<221> NAME/KEY: misc_feature
<222> LOCATION: (34)..(34)
<223> OTHER INFORMATION: can be a, c, g, u

<400> SEQUENCE: 13
nnnngauacc agccgaaagg cccuuggagc nnnn                              34
```

```
<210> SEQ ID NO 14
<211> LENGTH: 14
<212> TYPE: RNA
<213> ORGANISM: Artificial Sequence
<220> FEATURE:
<223> OTHER INFORMATION: Five Prime Handle

<400> SEQUENCE: 14
ggucuaaccc ucaa                                                         14

<210> SEQ ID NO 15
<211> LENGTH: 18
<212> TYPE: RNA
<213> ORGANISM: Artificial Sequence
<220> FEATURE:
<223> OTHER INFORMATION: Three Prime Handle

<400> SEQUENCE: 15
aaauagacag ccgaagcc                                                     18

<210> SEQ ID NO 16
<211> LENGTH: 106
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (30)..(30)
<223> OTHER INFORMATION: can be a, c, g, u
<220> FEATURE:
<221> NAME/KEY: misc_feature
<222> LOCATION: (31)..(31)
<223> OTHER INFORMATION: can be a, c, g, u
<220> FEATURE:
<221> NAME/KEY: misc_feature
<222> LOCATION: (32)..(32)
<223> OTHER INFORMATION: can be a, c, g, u
<220> FEATURE:
<221> NAME/KEY: misc_feature
<222> LOCATION: (33)..(33)
<223> OTHER INFORMATION: can be a, c, g, u
<220> FEATURE:
<221> NAME/KEY: misc_feature
<222> LOCATION: (60)..(60)
<223> OTHER INFORMATION: can be a, c, g, u
<220> FEATURE:
<221> NAME/KEY: misc_feature
<222> LOCATION: (61)..(61)
<223> OTHER INFORMATION: can be a, c, g, u
<220> FEATURE:
<221> NAME/KEY: misc_feature
<222> LOCATION: (62)..(62)
<223> OTHER INFORMATION: can be a, c, g, u
<220> FEATURE:
<221> NAME/KEY: misc_feature
<222> LOCATION: (63)..(63)
<223> OTHER INFORMATION: can be a, c, g, u

<400> SEQUENCE: 16
ggucuaaccc ucaaggaucg cggaagggan nnngauacca gccgaaaggc ccuuggagcn       60
nnngaaggug cggagaggag acgcgaucca aauagacagc cgaagc                    106

<210> SEQ ID NO 17
<211> LENGTH: 107
<212> TYPE: RNA
<213> ORGANISM: Artificial Sequence
<220> FEATURE:
<223> OTHER INFORMATION: Aptamer
<220> FEATURE:
<221> NAME/KEY: misc_feature
```

```
<222> LOCATION: (36)..(36)
<223> OTHER INFORMATION: can be a, c, g, u
<220> FEATURE:
<221> NAME/KEY: misc_feature
<222> LOCATION: (37)..(37)
<223> OTHER INFORMATION: can be a, c, g, u
<220> FEATURE:
<221> NAME/KEY: misc_feature
<222> LOCATION: (38)..(38)
<223> OTHER INFORMATION: can be a, c, g, u
<220> FEATURE:
<221> NAME/KEY: misc_feature
<222> LOCATION: (39)..(39)
<223> OTHER INFORMATION: can be a, c, g, u
<220> FEATURE:
<221> NAME/KEY: misc_feature
<222> LOCATION: (66)..(66)
<223> OTHER INFORMATION: can be a, c, g, u
<220> FEATURE:
<221> NAME/KEY: misc_feature
<222> LOCATION: (67)..(67)
<223> OTHER INFORMATION: can be a, c, g, u
<220> FEATURE:
<221> NAME/KEY: misc_feature
<222> LOCATION: (68)..(68)
<223> OTHER INFORMATION: can be a, c, g, u
<220> FEATURE:
<221> NAME/KEY: misc_feature
<222> LOCATION: (69)..(69)
<223> OTHER INFORMATION: can be a, c, g, u

<400> SEQUENCE: 17
ggucuaaccc ucaaggaucg cggaagggac ggugannnng auaccagccg aaaggcccuu      60
ggagcnnnng aaggagagga gacgcgaucc aaauagacag ccgaagc                  107

<210> SEQ ID NO 18
<211> LENGTH: 107
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (41)..(41)
<223> OTHER INFORMATION: can be a, c, g, u
<220> FEATURE:
<221> NAME/KEY: misc_feature
<222> LOCATION: (42)..(42)
<223> OTHER INFORMATION: can be a, c, g, u
<220> FEATURE:
<221> NAME/KEY: misc_feature
<222> LOCATION: (43)..(43)
<223> OTHER INFORMATION: can be a, c, g, u
<220> FEATURE:
<221> NAME/KEY: misc_feature
<222> LOCATION: (44)..(44)
<223> OTHER INFORMATION: can be a, c, g, u
<220> FEATURE:
<221> NAME/KEY: misc_feature
<222> LOCATION: (71)..(71)
<223> OTHER INFORMATION: can be a, c, g, u
<220> FEATURE:
<221> NAME/KEY: misc_feature
<222> LOCATION: (72)..(72)
<223> OTHER INFORMATION: can be a, c, g, u
<220> FEATURE:
<221> NAME/KEY: misc_feature
<222> LOCATION: (73)..(73)
<223> OTHER INFORMATION: can be a, c, g, u
<220> FEATURE:
<221> NAME/KEY: misc_feature
<222> LOCATION: (74)..(74)
<223> OTHER INFORMATION: can be a, c, g, u

<400> SEQUENCE: 18
``` ggucuaacccc ucaaggaucg cggaagggac ggugcggaga nnnngauacc agccgaaagg    60
cccuuggagc nnnngaagga gacgcgaucc aaauagacag ccgaagc                  107

<210> SEQ ID NO 19
<211> LENGTH: 123
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (44)..(44)
<223> OTHER INFORMATION: can be a, c, g, t
<220> FEATURE:
<221> NAME/KEY: misc_feature
<222> LOCATION: (45)..(45)
<223> OTHER INFORMATION: can be a, c, g, t
<220> FEATURE:
<221> NAME/KEY: misc_feature
<222> LOCATION: (46)..(46)
<223> OTHER INFORMATION: can be a, c, g, t
<220> FEATURE:
<221> NAME/KEY: misc_feature
<222> LOCATION: (47)..(47)
<223> OTHER INFORMATION: can be a, c, g, t
<220> FEATURE:
<221> NAME/KEY: misc_feature
<222> LOCATION: (74)..(74)
<223> OTHER INFORMATION: can be a, c, g, t
<220> FEATURE:
<221> NAME/KEY: misc_feature
<222> LOCATION: (75)..(75)
<223> OTHER INFORMATION: can be a, c, g, t
<220> FEATURE:
<221> NAME/KEY: misc_feature
<222> LOCATION: (76)..(76)
<223> OTHER INFORMATION: can be a, c, g, t
<220> FEATURE:
<221> NAME/KEY: misc_feature
<222> LOCATION: (77)..(77)
<223> OTHER INFORMATION: can be a, c, g, t
<220> FEATURE:
<221> NAME/KEY: promoter
<222> LOCATION: (107)..(123)
<223> OTHER INFORMATION: T7 promoter

<400> SEQUENCE: 19
gcttcggctg tctatttgga tcgcgtctcc tctccgcacc ttcnnnngct ccaagggcct    60
ttcggctggt atcnnnntcc cttccgcgat ccttgagggt tagacctata gtgagtcgta   120
tta                                                                 123

<210> SEQ ID NO 20
<211> LENGTH: 124
<212> TYPE: DNA
<213> ORGANISM: Artificial Sequence
<220> FEATURE:
<223> OTHER INFORMATION: aptamer
<220> FEATURE:
<221> NAME/KEY: misc_feature
<222> LOCATION: (39)..(39)
<223> OTHER INFORMATION: can be a, c, g, t
<220> FEATURE:
<221> NAME/KEY: misc_feature
<222> LOCATION: (40)..(40)
<223> OTHER INFORMATION: can be a, c, g, t
<220> FEATURE:
<221> NAME/KEY: misc_feature
<222> LOCATION: (41)..(41)
<223> OTHER INFORMATION: can be a, c, g, t
<220> FEATURE:
<221> NAME/KEY: misc_feature
<222> LOCATION: (42)..(42)
<223> OTHER INFORMATION: can be a, c, g, t

```
<220> FEATURE:
<221> NAME/KEY: misc_feature
<222> LOCATION: (69)..(69)
<223> OTHER INFORMATION: can be a, c, g, t
<220> FEATURE:
<221> NAME/KEY: misc_feature
<222> LOCATION: (70)..(70)
<223> OTHER INFORMATION: can be a, c, g, t
<220> FEATURE:
<221> NAME/KEY: misc_feature
<222> LOCATION: (71)..(71)
<223> OTHER INFORMATION: can be a, c, g, t
<220> FEATURE:
<221> NAME/KEY: misc_feature
<222> LOCATION: (72)..(72)
<223> OTHER INFORMATION: can be a, c, g, t
<220> FEATURE:
<221> NAME/KEY: promoter
<222> LOCATION: (108)..(124)
<223> OTHER INFORMATION: T7 promoter

<400> SEQUENCE: 20
gcttcggctg tctatttgga tcgcgtctcc tctccttcnn nngctccaag ggcctttcgg      60
ctggtatcnn nntcaccgtc ccttccgcga tccttgaggg ttagacctat agtgagtcgt     120
atta                                                                 124

<210> SEQ ID NO 21
<211> LENGTH: 124
<212> TYPE: DNA
<213> ORGANISM: Artificial Sequence
<220> FEATURE:
<223> OTHER INFORMATION: aptamer
<220> FEATURE:
<221> NAME/KEY: misc_feature
<222> LOCATION: (34)..(34)
<223> OTHER INFORMATION: can be a, c, g, t
<220> FEATURE:
<221> NAME/KEY: misc_feature
<222> LOCATION: (35)..(35)
<223> OTHER INFORMATION: can be a, c, g, t
<220> FEATURE:
<221> NAME/KEY: misc_feature
<222> LOCATION: (36)..(36)
<223> OTHER INFORMATION: can be a, c, g, t
<220> FEATURE:
<221> NAME/KEY: misc_feature
<222> LOCATION: (37)..(37)
<223> OTHER INFORMATION: can be a, c, g, t
<220> FEATURE:
<221> NAME/KEY: misc_feature
<222> LOCATION: (64)..(64)
<223> OTHER INFORMATION: can be a, c, g, t
<220> FEATURE:
<221> NAME/KEY: misc_feature
<222> LOCATION: (65)..(65)
<223> OTHER INFORMATION: can be a, c, g, t
<220> FEATURE:
<221> NAME/KEY: misc_feature
<222> LOCATION: (66)..(66)
<223> OTHER INFORMATION: can be a, c, g, t
<220> FEATURE:
<221> NAME/KEY: misc_feature
<222> LOCATION: (67)..(67)
<223> OTHER INFORMATION: can be a, c, g, t
<220> FEATURE:
<221> NAME/KEY: promoter
<222> LOCATION: (108)..(124)
<223> OTHER INFORMATION: T7 promoter

<400> SEQUENCE: 21
gcttcggctg tctatttgga tcgcgtctcc ttcnnnnget ccaagggcct ttcggctggt      60
atcnnnntct ccgcaccgtc ccttccgcga tccttgaggg ttagacctat agtgagtcgt     120
```

```
atta                                                                 124

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ggcttcggct gtctatttgg atc                                             23

<210> SEQ ID NO 23
<211> LENGTH: 37
<212> TYPE: DNA
<213> ORGANISM: Artificial Sequence
<220> FEATURE:
<223> OTHER INFORMATION: Primer

<400> SEQUENCE: 23
taatacgact cactataggt ctaaccctca aggatcg                              37
```

NUCLEIC ACID BASED BIOSENSOR AND METHODS THEREOF

CROSS-REFERENCE TO RELATED APPLICATIONS

This application claims priority to provisional application U.S. Ser. No. 62/924,907, filed Oct. 23, 2019, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 4, 2021, is named 2021-01-04_BURDEN_P12888 US01_SEQLISTING_ST25.txt and is 11,257 bytes in size.

FIELD OF THE INVENTION

The instant disclosure relates to nucleic acid molecules which comprise of at least one stem and/or loop structure that may bind to a reporter molecule, such as a fluorophores, and/or a target molecule, methods of making the nucleic acid molecules, methods to use the nucleic acid molecules as a biosensor, and kits comprising the nucleic acid molecules for practicing their method.

BACKGROUND OF THE INVENTION

Aptamers comprised of nucleic acids that may bind fluorogenic molecules are emerging as useful tools for basic and applied biology for use as biosensors. These aptamers may be genetically encoded like fluorescent proteins but enable observation at different levels. Also, unlike fluorescent proteins these aptamers are not natural and instead are engineered in the lab using various methods such as fluorescence or complex affinity based in vitro selections (Ellington et al., 1990, In vitro selection of RNA molecules that bind specific ligands. *Nature* 346: 818-822; Bock et al. 1992, Selection of single-stranded DNA molecules that bind and inhibit human thrombin. *Nature* 355: 564-566, both herein incorporated in their entirety). A high fluorescence signal above background is possible due to fluorescence enhancement of a second molecule upon binding to the aptamer.

The recently developed RNA Mango series of aptamers have the promising combination of tight binding to its ligand and significant fluorescence enhancement. The RNA Mango aptamers bind biotinylated derivatives of Thiazole Orange with low nanomolar KD and fluorescence enhancement of approximately 1,100-fold. There are currently several variants of the RNA Mango with subtle nucleotide sequence variations that lead to different ligand affinities and fluorescence enhancements (Dolgosheina et al., 2014, RNA Mango aptamer-fluorophore: a bright, high affinity, complex for RNA labeling and tracking. *ACS Chem Biol* 9(10):2412-2; Trachman et al., 2019, Structural basis for high-affinity fluorophore binding and activation by RNA Mango. *Nat Chem Biol* 13: 807-813; Autour et al., 2018, Fluorogenic RNA Mango aptamers for imaging small non-coding RNAs in mammalian cells. *Nat Commun* 9: 656, all herein incorporated in their entirety by reference). The structures of the original aptamer, termed Mango-I, is quite simple with a single base-paired stem capped by a three tiered G-quadruplex where the ligand binds.

Other fluorogenic aptamers, such as RNA Spinach and related aptamers, also have G-quadruplex ligand binding sites, but with more than one base-paired stem joined to the quadruple. These additional helical elements have been used in several applications that require more complex structures, such as the detection of RNA-RNA interactions and dual-aptamer allosteric RNA biosensors but lack the signal to background ratio of the Mango aptamers making them less sensitive and inferior biosensors, so much so that they may not be able to identify some targets when the target is in a low quantity. In addition, quadruplex flanking helices have been shown to modulate aptamer properties such as metal ion specificity.

Further, the simpler structure of RNA Mango-I is limiting to efforts to design more complex functionalities because it is unclear how to add additional nucleotide elements to the G-quadruplex core without disrupting ligand binding or if a switching effect could be achieved by the addition of additional nucleotides. Computational tools to predict quadruplex structures are advancing, but do not currently provide the ability to predict ligand affinity and fluorescence enhancement.

Research efforts are ongoing to improve the properties of both the ligands and RNA sequences, representing the nucleotides, in these fluorogenic aptamer systems to improve their functionality in vivo and in vitro. Therefore, there continues to be a need to design improved aptamers with a high signal to background noise ratio to enhance biosensors for in vitro and in vivo detections.

BRIEF SUMMARY OF THE INVENTION

Accordingly, the present disclosure relates to nucleic acid molecules related to the Mango aptamer. There are several varieties of Mango aptamers, such as the Mango-I aptamer, which traditionally has a single opened stem attached to a square shaped G-quadruplex core, wherein the G-quadruplex may bind a heterocyclic fluorophore, such as Thiazole Orange (TO1)-biotin (TO1B) bi-functional fluorescent molecule. The Mango aptamer, due to this square link shape, may be thought to have four edges, i, ii, iii, and iv, and four corners, i-ii, ii-iii, iii-iv, and iv-i. The open stem may comprise one of the corners of the G-quadruplex core. The present disclosure relates to the addition of one or more open or closed nucleotide stems to the corners of a Mango aptamer, wherein the additional stem includes a linker and a sensor domain. The sensor domain may bind to a target molecule, if the target molecule is present within the sample. The linker domain may effect a conformational change in the reporter domain in response to a target ligand molecule binding to the sensor domain which will allow the reporter to bind to the reporter domain.

An embodiment of the disclosure is a biosensor comprising of three components, a Mango core domain with an open stem, a linker, and a sensor domain. The linker and sensor domain may form an additional closed stem or open stem (split biosensor). A split biosensor may be comprised of either two different polynucleotides or a nicked closed stem. More complex designs may also be made through, by nonlimiting example, nucleotide origami where there may be two or more polynucleotides comprising the biosensor. In a further embodiment, the three components are modular so that once a specific domain is designed, it may be easily switched to develop a biosensor with different properties.

In another further embodiment the open stem of the Mango core domain is positioned on an adjacent corner to at least one closed stem of a linker and sensor domain. In a different embodiment, the open stem and another closed stem are positioned on opposite corners of each other on the Mango core domain. In further embodiments, the biosensor may have two or more closed stems or three closed stems. The closed stems may bind to the same or different target ligands and may have the same or different linkers. The additional open stems may be on adjacent or opposite corners of the Mango core.

In another embodiment, the biosensor may contain additional functional units, such as, but not limited to, promoters or handles, attached to the open end.

In another embodiment, a plasmid comprises the biosensor and additional functional units, such as promoters, which will express the biosensor.

A different embodiment of the disclosure is a method of selecting a biosensor of the disclosure which binds to a defined target. For a biosensor to function properly, it must be able to detect a target ligand in a sample, and then provide a discriminating signal. The method comprises obtaining a library of randomly generated sequences, which comprise the Mango core, different linkers, and at least one sensor domain; subjecting the library to one or more rounds of negative and positive selection; and measuring the change in brightness from an unbound to a bound state. The negative selection depletes sequence which only bind to the reporter, for example TO1B, in the absence of the target ligand. The positive selection enriches for the binding of the reporter in the presence of the target ligand. However, the presence of the target ligand does not make it essential that the reporter will bind to the reporter domain.

In an embodiment of the selection, while the number of rounds of selection may be determined by one skilled in the art, to save costs the number of positive and negative selection rounds is less than about 10. In a further embodiment, a following round of selection is performed on the results from the prior round. In another embodiment, the negative selection is performed before the positive selection.

In some embodiments, the same type of selection is performed on the results of the prior round. In other embodiments, the type of selection is alternated between rounds. In another embodiment, one or negative rounds is followed by one or more positive rounds or one or more positive rounds is followed by one or more negative rounds.

In other embodiments, either positive or negative selection is performed.

In another embodiment, the pool may be split into two after partial selection, with the first split being subjected to a final round of negative selection and the second split being subjected to a final round of positive selection, the two splits sequenced, and the number of specific sequences counted. The ratio between the negative and positive split may then be used to determine biosensors according to this disclosure.

In another aspect of the disclosure, an embodiment comprises a method of binding the biosensors of the invention to a target in a sample. The method comprises of introducing into a sample a biosensor of the disclosure and the reporter; and incubating the sample to allow for binding to a target ligand. In another embodiment the sample is then excited by the appropriate wavelengths to allow for the amount of the target ligand to be quantified by measuring the difference in brightness of the biosensor in the sample to a control biosensor.

In another embodiment, a fluorescent label is further introduced into the sample. The quantity of target ligand may be obtained by comparing the signal from the biosensor to the fluorescent label.

In another embodiment, the method further includes fixing a sample prior to introducing the biosensor and reporter into the sample. This may be done to locate the position of a target within a sample, such as, but not limited to, subcellular structures, RNA, or cells, such as bacteria cells within an environmental sample.

In another aspect of the disclosure, an embodiment comprises a kit which may be used to binding a desired target in a sample. The kit may comprise of the biosensor and/or a nucleic acid comprising the biosensor and additional functional regions, such as, but not limited to, one or more promoter regions. In additional embodiments, the kit may further comprise of the reporter molecule, by way of non-limiting example TOB1; buffers; solvents, such as but not limited to polar or organic solvents; and/or instructions.

While multiple embodiments are disclosed, still other embodiments of the present invention will become apparent to those skilled in the art from the following detailed description, which shows and describes illustrative embodiments of the invention. Accordingly, the drawing sand detailed description are to be regarded as illustrative in nature and not restrictive.

DETAILED DESCRIPTION

Figure 1A:
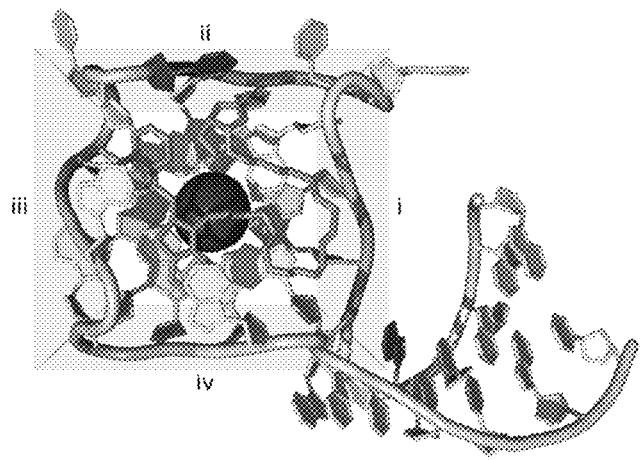
FIG. 1A is a schematic representation of the crystal structure of a single strand Mango I aptamer bound to TO1-biotin with the edges of the G quadruplex labeled i, ii, iii, and iv.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4% This applies regardless of the breadth of the range.

Other than in the operating examples, or where otherwise indicated, all numbers expressing quantities of ingredients or reaction conditions used herein are to be understood as being modified in all instances by the term "about".

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

The term "isolated" is used to indicate that a cell, peptide or nucleic acid is separated from its native environment. Isolated peptides and nucleic acids may be substantially pure, i.e. essentially free of other substances with which they may bound in nature.

The terms "nucleic acid," "polynucleotide," and "oligonucleotide" are used interchangeably and refer to a polymer of deoxyribonucleotide, ribonucleotide, or analogs thereof, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T. A nucleic acid can be single-stranded or double-stranded. A single-stranded nucleic acid can have double-stranded regions and a double-stranded nucleic acid can have single-stranded regions.

As used herein, a "nucleotide" is any nucleoside linked to a phosphate group. The nucleoside may be natural, including but not limited to, any of cytidine, uridine, adenosine, guanosine, thymidine, inosine (hypoxanthine), or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, which act as a linker group lacking a base or be a nucleotide analog. As used herein, nucleotide is used interchangeably with "nucleic acid."

As used herein, "nucleotide duplex" is when two strands of complement nucleotide oligomers complementary bind to each other. The two strands may be part of the same nucleotide molecule or separate nucleotide molecules.

The nucleotides making up the biosensors may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tatramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivatives at positions 2, 3, and 4, and fluoro derivates at position 2 and 3; purine/pyrimidine mimics, such as but not limited to azole hetercyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or theino pyridiones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or N6-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2-oxophenoxazine, pyrrolo-dC and derivatives, 3-MI, 6-MI, 6-MAP, or furan-modified bases.

Non-limiting examples of nucleotide analogs include, but are not limited to, phosorothioate nucleotides, 2'-O-methyl ribonucleotides, 2'-O-methoxy-ethyl ribonucleotides, peptide nucleotides, N3'-P5' phosphoroamidate, 2'-fluoro-arabino nucleotides, locked nucleotides (LNA), unlocked nucleotides (UNA), morpholino phosphoroamidate, cyclohexene nucleotides, tricyclo-deoxynucleotides, or triazole-linked nucleotides.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, amino acids include natural or unnatural amino acids. Thus, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways. Exemplary amino acids amenable to the present invention include, but are not limited to, alanine; argnine; asparagine; aspartic acid; cysteine; glutamic acid; glutamine; glycine; histadine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; y-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; γ-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (Glp); α-aminoisobutyric acid (αAib); γ-aminobutyric acid (γAbu); α-aminobutyric acid (αAbu); .αγ-aminobutyric acid (αγAbu); 3-pyridylalanine (Pal); Isopropyl-α-$N^e$-lysine (ILys); Napthyalanine (Nal); α-napthyalanine (α-Nal); β-napthyalanine (β-Nal); Acetyl-β-napthyalanine (Ac-β-napthyalanine); napthyalanine; NE-picoloyl-lysine (PicLys); 4-halo-Phenyl; 4-pyrolidylalanine; isonipecotic carboxylic acid (inip); β-amino acids; and isomers, analogs and derivatives thereof. One of skill in the art would know that this definition includes, D- and L-amino acids, α- and β-amino acids, chemically modified amino acids, naturally occurring non-proteogenic amino acids, rare amino acids, and chemically synthesized compounds that have properties known in the art to be characteristic of an amino acid.

A "ligand" is a type of molecule that is recognized by a receptor or aptamer and either causes the receptor to signal, an "agonist," or prevents the receptor to signal, an "antagonist." A "target ligand" is the ligand which is to be assayed within a sample by the biosensor and may be, by nonlimiting example, a small molecule, a ribonuclear protein, a protein, a bacterial cell wall or membrane, a viral coat, an organic or inorganic molecule, a macromolecular complex, or an oligonucleotide. The terms "target ligand" and "target molecule" are used interchangeably herein.

As used herein, a "small molecule" is any low molecular weight (<900 daltons) organic compound with a size on the order of 1 nm.

A "macromolecular complex" refers to a collection of molecules that may be random, ordered or partially ordered in their arrangement. The term encompasses biological organisms such as bacteriophage, viruses, bacteria, unicellular pathogenic organisms, multicellular pathogenic organisms and prokaryotic or eukaryotic cells. The term also encompasses non-living assemblages of molecules, such as liposomes, microcapsules, microparticles, magnetic beads and microdevices. The only requirement is that the complex contains more than one molecule. The molecules may be identical or may differ from each other.

A "receptor" may be peptides, proteins, glycoproteins, lipoproteins, epitopes, antibodies, lipids, carbohydrates, multi-molecular structures, a specific conformation of one or more molecules and a morphoanatomic entity that has a binding affinity for a specific group of chemicals or molecules, such as other proteins or viruses. Upon recognition and binding of the chemical or molecule, the receptor can cause some form of signaling or other process within a cell to respond to the chemical or molecule. Optionally, the chemical or molecule can cause a receptor to stop functioning property and shut off processes.

"Ribonuclear protein" (RNP) is an association of a RNA-binding protein and a ribonucleic acid.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence but need not be directly adjacent to it. For example, an enhancer is a transcriptional regulatory sequence that is operatively linked to a coding sequence, even though they are not contiguous.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

In the present context, the term "expression vector" covers a DNA molecule, linear or circular, that comprises a segment encoding a polypeptide of the invention, and which is operably linked to additional segments that provide for its transcription.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; U.S. Pat. No. 5,591,439). Examples of non-viral vectors include, but are not limited to, liposomes, polyamine derivatives of DNA, and the like.

The term "host cell", as used herein, includes any cell type which is susceptible to transformation with a nucleic acid construct. By "host cell" is meant a cell which contains a vector and supports the replication and/or expression of the vector. Host cells may be prokaryotic cells such as *E. coli*, or eukaryotic cells such as yeast, insect, amphibian, or mammalian cells.

As used herein "promoter" includes reference to a region of DNA upstream from the start of transcription and involved in recognition and binding of RNA polymerase and other proteins to initiate transcription.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

As used herein, a "sample" is a small part or quantity intended to represent the whole. For example, an environmental sample could be a small quantity of soil from a field or water from a lake. It could also be a blood or tissue sample from a human or animal. Sometimes the sample is purified to select an even smaller or more specific sample, such as isolating RNA, DNA, or protein from a blood or tissue sample.

Biosensors

The biosensor comprises of three or more domains in a modular design. The domains comprise a reporter domain, one or more linker domains, and one or more sensor domains. A biosensor comprises of one or more strands of polynucleotides and may be RNA, DNA, PNA, LNA, or UNA. While typically made of RNA, these other nucleic acids may be used to alter the rigidity of the biosensor. For example, UNA may be used to make a more relaxed backbone while LNA may make a more stable biosensor compared to a biosensor comprised of RNA.

Reporter Domain

The reporter domain comprises a Mango core as described in WO2018/198013 (herein incorporated in its entirety). The Mango core comprises of two section, an open stem and a G-quadruplex which binds to fluorophore. While the biosensor may be any nucleotide, such as DNA, RNA, UNA, PNA, or LNA, the core sequence may be represented by the RNA sequence: 5'-GG@($T_1$/WGW)GG($\#_1$H/WG)WGGN@($\#_2$/-)G($T_2$/H)GNH(AN@$T_3$/G)-3' (a, c, g) where:

represents no nucleotide (gap);
  K represents U or G;
  S represents C or G,
  R represents A or G;
  W represents A or U;
  H represents A, C, or U;
  N represents A, C, G, or U; and
  @ represents N or no nucleotide;
  wherein/between the brackets ( ) represents an alternative; and wherein $T_1$ represents any nucleotide, $T_2$ and $T_3$ being defined as follows:
    when $T_1$ is A, $T_2$ can be either A, G or U; and
      when $T_1$ is A and $T_2$ is A, then $T_3$ is U;
      when $T_1$ is A and $T_2$ is G, then $T_3$ is U; and
      when $T_1$ is A and $T_2$ is U, then $T_3$ is A or U; or
    when $T_1$ is C, $T_2$ can be either G or U; and
      when $T_1$ is C and $T_2$ is G, then $T_3$ is C or G; and
      when $T_1$ is C and $T_2$ is U, then $T_3$ is G; or
    when $T_1$ is G, $T_2$ can be either G or C, and $T_3$ is C; or
    when $T_1$ is U, $T_2$ can be either A or C; and
      when $T_1$ is U and $T_2$ is A, then $T_3$ is A or U; and
      when $T_1$ is U and $T_2$ is C, then $T_3$ is A;
  wherein $\#_1$ and $\#_2$ represents any nucleotide pair such that:
    when $\#_1$ is A, then $\#_2$ represents A, C, G, or U; or
    when $\#_1$ is C, then $\#_2$ is C; or
    when $\#_1$ is G, then $\#_2$ is G; or
    when $\#_1$ is U, then $\#_2$ represents A, G, or U.
  wherein $\#_1$ and $\#_2$ represents any nucleotide pair such that:
    when $\#_1$ is A, then $\#_2$ represents A, C, G, or U; or
    when $\#_1$ is C, then $\#_2$ is C; or
    when $\#_1$ is G, then $\#_2$ is G; or
    when $\#_1$ is U, then $\#_2$ represents A, G, or U,
wherein the aptamer adopts a determined tridimensional conformation which is a fluorophore binding conformation, said aptamer when it adopts the fluorophore binding conformation being liable to interact with a fluorophore; wherein the aptamer further comprises, contiguous with the active core sequence, a 5' leader sequence attached, or operably linked to (by covalent bound, i.e. phosphodiester bound), to the 5' terminus of the active core and a 3' tail sequence attached, or operably linked to (by covalent bridge mentioned below), to the 3' terminus of the active core, wherein the 5' leader sequence and the 3' tail sequence together mediate the juxtaposition of the 5' terminus of the active core and the 3' terminus of the active core when the aptamer is the fluorophore binding conformation (see FIGS. 1A and 1B).

The G-quadruplex has been further labeled by the edges in this disclosure, being numbered: i, ii, iii, and iv (see FIG. 1A). There are nucleotides not involved in G-quartets, which bind the fluorophore, at the corners of the G-quadruplex, termed loops, where two edges meet. Corners are designated by the two edges which comprise the corner, for example corners i-ii and ii-i are both synonymous for the corner between edges i and ii (see FIG. 1B). As shown in FIGS. 1B and 2A-2H, corner i-ii lacks an A/U flap present at the other corners. The order of the corner edges is not important but may be used for additional clarification where noted.

The G-quadruplex may then bind to a heterocyclic fluorophore represented in Formula I or II:

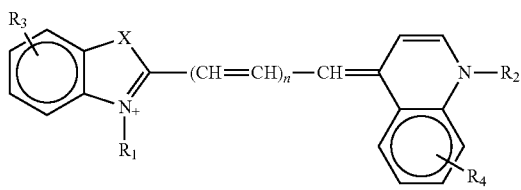

I wherein:
X represents O, S, Se, or $C(CH_3)_n$;
$R_1$ and $R_2$ represent an alkyl having form 1-6 carbons;
$R_3$ is either a fused benzene, an alkyl having 1-6 carbons, a methoxy or H;
$R_4$ is an alkyl having 1-6 carbons, a methoxy or H; and
n=zero or an integer from 1-6;

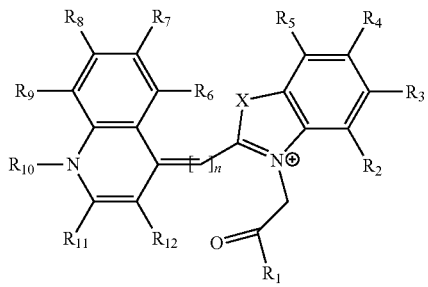

II wherein:
X represents O, S, or Se;
$R_1$ represents any substituent
$R_2$-$R_{12}$ represents independently an alkyl having 1-6 carbons, H, F, Cl, Br, linear polymer, or extended heterocycles; and
n=zero or an integer from 1-5, preferably 1, 3, or 5.

The terms "alkyl" and "heteroalkyl" each includes any reasonable combination of the following: (1) saturated alkyls as well as unsaturated alkyls (e.g. alkenyls and alkynyls); (2) linear or branched; (3) acyclic, cyclic (aromatic or nonaromatic) or multi-cyclic (fused rings, multiple non-fused rings or a combination thereof); and (4) unsubstituted or substituted. For example, an alkyl or heteroalkyl (i.e. "alkyl/heteroalkyl") may be saturated, branched and cyclic, or unsaturated, branched and cyclic, or linear and unsaturated, or any other reasonable combination according to the skill of the person of skill in the art. Where the size of the alkyl/heteroalkyl is specified as $X_1$-Xz, where z is any integer larger than 1 (e.g. 15, 18, 30, 100 or the like), it will be understood that the alkyl/heteroalkyl comprises at least 3 carbons and heteroatoms so as to form a ring. If unspecified, the size of the alkyl/heteroalkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 carbons and heteroatoms in length, subject to the common general knowledge of the person of skill in the art.

For convenience, unless otherwise specified the term "alkyl" shall without limitation include "alkylenyl" unless the context of its use clearly excludes alkylenyls, and vice versa. For example, but without limitation, where $R^1$, $R^2$, and $R^3$ in $R^1$-$R^2$-$R^3$ are identified as alkyl groups, it will be understood that $R^2$ is an alkylenyl group and, similarly, $R^1$ and $R^3$ do not include alkylenyl groups.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

As used herein, the term "saturated" when referring to a chemical entity may be used as it is normally understood to a person of skill in the art and generally refers to a chemical entity that comprises only single bonds. Non-limiting examples of a saturated $C_1$-$C_{15}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, l-ethyl-2-methylpropyl, 1,1,2-trimethylpropyl, 1,1,2-triethylpropyl, 1, 1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{15}$ alkenyl group may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{15}$ alkynyl group may include ethynyl, propynyl, butynyl, pentynyl, hexynyl, heptynyl, octynyl, nonynyl and decynyl. Without limitation, the above-defined saturated $C_1$-$C_{15}$ alkyls, $C_2$-$C_{15}$ alkenyls and $C_2$-$C_{15}$ alkynyls are all encompassed within the term "X1-X15 alkyl", as used herein.

Without limitation, the term "X1-X15 heteroalkyl" would encompass each of the above-defined saturated $C_1$-$C_5$ alkyls, $C_2$-$C_{15}$ alkenyls and $C_2$-$C_{15}$ alkynyls, where one or more of the carbon atoms is independently replaced with a heteroatom. The person of skill in the art would understand that various combinations of different heteroatoms may be used.

Unless explicitly stated otherwise, the terms "aryl" and "heteroaryl" each includes any reasonable combination of the following: (1) cyclic or multi-cyclic (fused rings, multiple non-fused rings or a combination thereof); and (2) aromatic (i.e. unsaturated rings) or nonaromatic (i.e. saturated rings); and (3) unsubstituted or substituted. Non-limiting examples of aryls or heteroaryls (i.e. "aryl/heteroaryl") include: phenyl, naphthyl, thienyl, indolyl, pyridyl and the like. If unspecified, the size of the aryl/heteroaryl is what would be considered reasonable to the person of skill in the art. For example, but without limitation, if unspecified, the size of an aryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroaryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 carbons and heteroatoms in length, subject to the common general knowledge of the person of skill in the art. It is noted that an aryl or heteroaryl may have all or only a portion of its skeleton or main chain bonded in such a way so as to form a 'loop', circle or ring of atoms bonded together. That is, the aryl/heteroaryl may comprise linear or branched chains of carbons/heteroatoms that are not part of a ring or loop.

As used herein, the term "substituted" is used as it would normally be understood to a person of skill in the art and generally refers to a compound or chemical entity that has one chemical group replaced with a different chemical group. Unless otherwise specified, a substituted alkyl may be an alkyl in which one or more hydrogen atom(s) may be/are replaced with one or more atom(s) that may be/are not hydrogen(s). For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, heteroalkyl, aryl, heteroaryl and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl, trihalomethyl.

As used herein, the term "unsubstituted" is used as it would normally be understood to a person of skill in the art. Non-limiting examples of unsubstituted alkyls include methyl, ethyl, tert-butyl, and pentyl. The expression "optionally substituted" is used interchangeably with the expression "unsubstituted or substituted".

The fluorophore is preferably Thiazole Orange (TO1)-biotin (TO1B) bi-functional fluorescent molecule.

The Mango core and the fluorophore have a low dissociation constant, $K_d$, with the fluorophores. The $K_d$ is at least about 0.5 µM, at least about 0.7 µM, at least about 1.0 µM, at least about 1.5 µM, or at least about 2.0 µM. While a low $K_d$ may generally be an indicator of a biosensor, it has been surprisingly found that the biosensors of the instant application do not show a perfect correlation with $K_d$ in predicting biosensors with larger shifts in their brightness between a bound and unbound state. Without being bound by theory, it may be easier to stabilize a dye than it is to enhance fluorescence through an allosteric mechanism.

The Mango core advantageously, has a fluorophore binding affinity of at least about 400 nM, about 300 nM, about 200 nM, about 100 nM, about 50 nM, about 40 nM, about 30 nM, about 20 nM, about 10 nM, about 5 nM, about 1 nM, or about 0.5 nM when the core is in a fluorophore binding conformation. More advantageously, the invention relates to the biosensor according to the disclosure, wherein the fluorophore-Mango core complex has a brightness of at least 7,000 M/cm, 8,000 M/cm, 9,000 M/cm, 10,000 M/cm, or 43,000 M/cm. Further the fluorophore-Mango core has a fluorescent lifetime of at least 1 ns, or at least 2 ns, or at least 3 ns, or at least 4 ns or at least 5 ns, or at least 6 ns, or in the range of 1-6 ns, i.e. 1, or 2, or 3, or 4, or 5 or 6 ns.

Linker Domain

The terms "linker," "linker domain," "communication domain," and "linker region" are used interchangeably herein. The linker domain is positioned between the reporter and target domain. Signal transduction happens between the target domain and the reporter domain via the linker domain. As the target molecule is bound by the nucleic acid strand it induces a conformational change through the communication domain to either allow the dye to be bound in the reporter domain or to alter the signal from the bound fluorophore within the reporter domain. It is known that setting the size of the open stem on the Mango core to a length of 5 paired nucleotides will reduce florescence and at removing the stem altogether will suppress the fluorescent ability of the Mango core. However, it has previously been unknown if another stem could be placed onto the Mango core and have the Mango core still retain its fluorophore binding properties, and if so, if length would be a factor.

The linker may be about 16 nucleotides or less (for example 8 nucleotides per side), such as about 20 nucleotides or less, about 30 nucleotides or less, or about 40 nucleotides or less. Preferably, the linker domain is between about 2 and about 14 nucleotides, between about 4 and about 12 nucleotides, or between about 6 and about 10 nucleotides. The exact length may be determined by the needs of the targeting domain. The linker has preferably a symmetrical design so that half of the linker is one either side of the target domain, for example a about 16 nucleotide long linker domain would have two oligonucleotides of eight bases, one on either side flanking the target domain. However, the linker domain may be asymmetrical, i.e. having different numbers of nucleotides on each side of the stem.

The sequence can be generated randomly or may be selected. If randomly generated, libraries may be created comprising of $4^n$, where n is the number of nucleotides, unique sequences because the two sides of the linker domain may contain mismatches. These libraries are abbreviated as Nn libraries, where n is the number of nucleotides used in the construction of the library. If using Nn libraries of sufficient size, care should be taken to ensure necessary motifs are not duplicated between the linker domain and target domain. By way of non-limiting example, the necessary GAAA tetraloop-like motif may be omitted from a theophylline aptamer in the target domain if using an N8 or larger library as at least some of the linker domains would contain this motif.

The linker domain may or may not be positioned in such a way as to alter the binding of either reporter or target domain for their respective targets. The linker domain may be attached to either the reporter domain or the target domain in such a way to partially destabilize either binding pockets but without destroying the binding pocket ability. For example, the linker may be coupled to a truncated target domain with a single base pair on the end of the conserved binding pocket in order to partially reduce the binding of the target domain to its target.

The linker domain are attached to the reporter domain at the corners of the G-quadruplex. These positions are abbreviated herein as A, B, or C in a clockwise direction from the open stem of the reporter domain (for example, see FIGS. 4A-4C). If a single linker domain is attached, it is preferably in the B configuration.

Target Domain

One or more target domains are attached through one or more linker domains to the reporter domain. Together, the linker domain and the target domain form an additional stem on the reporter domain. Identifying suitable target domain comprising of a polynucleotide basically involves selecting polynucleotides that bind a particular target molecule with sufficiently high affinity (e.g., $K_d \leq 500$ nM when not reduced by the linker domain) and specificity from a pool or library of nucleic acids containing a random region of varying or predetermined length. For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," Nature 346:818-822 (1990); and Tuerk and Gold, "Systematic Evolution of Ligands by Exponential Enrichment: RNA Ligands to Bacteriophage T4 DNA Polymerase," Science 249:505-510 (1990), each of which is hereby incorporated by reference in their entirety. An established template-primer system (Bartel et al., "HIV-I Rev Regulation Involves Recognition of Non-Watson-Crick Base Pairs in Viral RNA," Cell 67:529-536 (1991), which is hereby incorporated by reference in its entirety) can be adapted to produce oligonucleotides having a stretch of about 38-40 random bases sandwiched between 5' and 3' constant regions.

One or more target domains may be attached to each linker domain. If more than one target domain is used, they may either bind to the same or different targets. Multiple target domains may work independently or together to effect an allosteric change in the biosensor.

The target molecule of interest can be any biomaterial or small molecule including, without limitation, proteins, nucleic acids (RNA or DNA), lipids, oligosaccharides, carbohydrates, small molecules, hormones, cytokines, chemokines, cell signaling molecules, metabolites, organic molecules, and metal ions. The target molecule of interest can be one that is associated with a disease state or pathogen infection.

In an embodiment, the target domain binds specifically to a target nucleic acid via hybridization (e.g., Watson-Crick base-pairing). Thus, the second domain has a nucleotide sequence that is sufficiently complementary to its target nucleic acid so as to hybridize under appropriate conditions with a target nucleic acid molecule that is physiologically found within a cell or within a biological sample. Upon hybridization between the second domain and the target, and the binding of the first domain to a fluorophore (introduced to the sample or cell), the target nucleic acid molecule is effectively labeled by the fluorophore. Presence of the target nucleic acid therefore can be detected based on the presence of fluorescence by the particular fluorophore employed.

Protein or polypeptide targets can be any length, and can include, without limitation, phosphoproteins, lipid-modified proteins, nitrosylated proteins, sulfenated proteins, acylated proteins, methylated proteins, demethylated proteins, C-terminal amidated proteins, biotinylated proteins, formylated proteins, gamma-carboxylated proteins, glutamylated proteins, glycylated proteins, iodinated proteins, hydroxylated proteins, isoprenylated proteins, lipoylated proteins (including prenylation, myristoylation, farnesylation, palmitoylation, or geranylation), proteins covalently linked to nucleotides such as ADP ribose (ADP-ribosylated) or flavin, oxidated proteins, proteins modified with phosphatidylinositol groups, proteins modified with pyroglutamate, sulfated proteins, selenoylated proteins, proteins covalently linked to another protein (including sumoylation, neddylation, ubiquitination, or ISGylation), citrullinated proteins, deamidated proteins, eliminylated proteins, disulfide bridged proteins, proteolytically cleaved proteins, proteins in which proline residues have been racemized, any peptides sequences that undergo the above mentioned modifications, and proteins which undergo one or more conformational changes. In addition, proteins or peptides that possess a mutation can be distinguished from wildtype forms. Complexes of two or more molecules include, without limitation, complexes have the following interactions: protein-protein, protein-cofactor, protein-inhibiting small molecules, protein-activating small molecules, protein-small molecules, protein-ion, protein-RNA, protein-DNA, DNA-DNA, RNA-DNA, RNA-RNA, modified nucleic acids-DNA or RNA, aptamer-aptamer. In addition, nucleic acids that possess a mutation can be distinguished from wildtype forms.

Nucleic acid targets can be any type of nucleic acid including, without limitation, DNA, RNA, LNA, PNA, UNA, genomic DNA, viral DNA, synthetic DNA, DNA with modified bases or backbone, mRNA, noncoding RNA, PIWI RNA, termini-associated RNA, promoter-associated RNA, tRNA, rRNA, microRNA, siRNA, post-transcriptionally modified RNA, synthetic RNA, RNA with modified bases or backbone, viral RNA, bacteria RNA, RNA aptamers, DNA aptamers, ribozymes, and DNAzymes.

Lipid targets include, without limitation, phospholipids, glycolipids, mono-, di-, tri-glycerides, sterols, fatty acyl lipids, glycerolipids, glycerophospholipids, sphingolipids, sterol lipids, prenol lipids, saccharolipids, polyketides, eicosanoids, prostaglandins, leukotrienes, thromboxanes, N-acyl ethanolamine lipids, cannabinoids, anandamides, terpenes, and lipopolysaccharides.

Small molecule targets include, without limitation, carbohydrates, monosaccharides, polysaccharides, galactose, fructose, glucose, amino acids, peptides, nucleic acids, nucleotides, nucleosides, cyclic nucleotides, polynucleotides, vitamins, drugs, inhibitors, single atom ions (such as magnesium, potassium, sodium, zinc, cobalt, lead, cadmium, etc.), multiple atom ions (such as phosphate), radicals (such as oxygen or hydrogen peroxide), and carbon-based gases (carbon dioxide, carbon monoxide, etc.).

Targets can also be whole cells or molecules expressed on the surface of whole cells. Exemplary cells include, without limitation, cancer cells, bacterial cells, or normal cells. Targets can also be viral particles.

Additional Groups

Additional oligonucleotides may also be attached the biosensor. By way of non-limiting example these additional oligonucleotides may be handles, barcodes, or promoters. These additional groups generally aid in the sequencing of the biosensor; in the production of the biosensor; or in the identification of the biosensor. For example, a T7 promoter may be attached to the biosensor prior to for the production of an RNA biosensor encoded by a double stranded DNA oligonucleotide.

Biosensor Synthesis

Due to their small size, any known method may be used to synthesize the biosensors. By way of nonlimiting example, the biosensor may be produced using any method of synthetic oligonucleotide syntheses, preferably solid-state synthesis; PCR amplification; or production in a cell. If produced in a cell, a host cell may be transformed with an expression vector comprising the biosensor operantly linked to a promoter capable of expressing the biosensor within the host cell.

While the biosensor of the present invention can be synthesized from chemical precursor, they also can be prepared either in vitro or in vivo using recombinant templates or constructs, including transgenes, that encode the biosensors of the present invention. Whether using in vitro transcription or transgenes suitable for expression in vivo, these genetic constructs can be prepared using well known recombinant techniques.

A further aspect of the present invention relates to a constructed DNA molecule that includes a first region encoding an RNA aptamer molecule of the invention.

According to one embodiment, the constructed DNA molecule encodes an RNA fusion product. Such a product is formed by joining together one piece of DNA encoding an RNA molecule of interest and a second piece of DNA encoding biosensor that binds specifically to a fluorophore of the invention, and which may bind the RNA molecule of interest, the protein produced from the RNA of interest, or a downstream effect caused by the introduction of the RNA of interest into a host cell.

According to another embodiment, the constructed DNA molecule encodes a biosensor of the disclosure, which is formed by joining together one piece of DNA encoding a target domain that is specific for a target ligand and a second piece of DNA encoding a receptor domain that binds specifically to a fluorophore, and a third piece of DNA encoding the linker domain.

According to yet another embodiment, the biosensor may be made in a modular format though preparing an empty construct for preparation of specific domains of the biosensor. Such an empty construct includes a DNA sequence encoding one or more of the reporter, linker, and/or target domain(s), along with appropriate regulatory sequences (discussed below), and a restriction enzyme insertion site that can be used for subsequent insertion of a desired DNA molecule, which may encode the remaining domains. The restriction enzyme insertion site can include one or more enzymatic cleavage sites to facilitate insertion of virtually any DNA coding sequence as desired. The restriction enzyme insertion site is preferably located between the promoter sequence and the aptamer-encoding DNA sequence.

According to a further embodiment, the constructed DNA molecule encodes a biosensor or the disclosure, however, within the region encoding the biosensor, an intron is positioned therein. This spatially segregates the biosensor-encoding regions, whereby transcription in the absence of a proper spliceosome will not afford a functional aptamer molecule. In the presence of a proper spliceosome, excision of the intron from a transcript of the constructed DNA molecule affords the biosensor of the disclosure. This will allow the biosensor to bind to the fluorophore to induce fluorescence.

In an alternative embodiment, the sequences within the intron contribute to the reporter domain, whereby prior to splicing the RNA molecule is capable of exhibiting fluorescence when bound to the fluorophore. However, in the presence of a proper spliceosome, splicing of the RNA molecule destroys the reporter domain, thereby inhibiting fluorescence.

While the biosensors may be prepared with any nucleotide, RNA biosensors may be made from DNA molecules, such as expression vectors, in vitro or in vivo. Preparation of the DNA molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the constructs of this disclosure. Once the expression vector or the biosensor of the present disclosure has been constructed, it can be incorporated into host cells as described infra. Transcription of the DNA molecule of the present invention is often dependent upon the presence of a promoter, which is a DNA sequence that directs the binding of RNA polymerase and thereby promotes RNA synthesis. Accordingly, the DNA molecule of the present invention may include a promoter operably coupled to the first region to control expression of the RNA aptamer. Because not all polymerases require promoters, the promoter sequence is optional.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). Depending on the application, it may be desirable to use strong promoters in order to obtain a high level of transcription. For instance, when used simply as a label high expression levels may be preferred, whereas to assess transcript behavior it may be desirable to obtain lower levels of expression that allow the cell to process the transcript.

Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the RNA aptamer, but also in vivo production in cultured cells or whole organisms, as described below. Because in vivo production can be regulated genetically, another suitable class of promoters is an inducible promoter which induces transcription of the DNA molecule in response to specific conditions, thereby enabling expression of the RNA aptamer as desired (i.e., expression within specific tissues, or at specific temporal and/or developmental stages). The various promoter types can be driven by RNA polymerases I, II, or III.

Suitable promoters for use with the constructed DNA molecule of the present invention include, without limitation, a T7 promoter, a SUP4 tRNA promoter, an RPRI promoter, a GPD promoter, a GALI promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," Nucleic Acids Res. 15(21): 8783-8798 (1987), which is hereby incorporated by reference in its entirety). The T7 RNA polymerase can also be used in mammalian and bacterial cells to produce very high levels of RNA. The SUP4 tRNA promoter and RPRI promoter are driven by RNA polymerase III of the yeast *Saccharomyces cerevisiae*, and suitable for high level expression of RNA less than 400 nucleotides in length (Kurjan et al., Mutation at the Yeast SUP4 tRNAtyr Locus: DNA Sequence Changes in Mutants Lacking Suppressor Activity," Cell 20:701-709 (1980); Lee et al., "Expression of RNase P RNA in *Saccharomyces cerevisiae* is Controlled by an Unusual RNA Polymerase III Promoter," Proc. Natl. Acad. Sci. USA 88:6986-6990 (1991), each of which is hereby incorporated by reference in its entirety). The glyceraldehyde-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," Gene 32:263-274 (1984), which is hereby incorporated by reference in its entirety). The galactokinase (GALI) promoter in yeast is a highly inducible promoter driven by RNA polymerase II (Johnston and Davis, "Sequences that Regulate the Divergent GALI-GALI0 Promoter in *Saccharomyces cerevisiae*," Mal. Cell. Biol. 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," Proc. Natl. Acad. Sci. USA 81:7318-7322 (1984), which is hereby incorporated by reference in its entirety).

Initiation of transcription in mammalian cells requires a suitable promoter, which may include, without limitation, -globin, GAPDH, -actin, actin, Cstf2t, SV40, MMTV, metallothionine-1, adenovirus Ela, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues. Any of a variety of tissue-specific promoters can be selected as desired.

For gene expression in plant cells, suitable promoters may include, without limitation, nos promoter, the small subunit ribulose bisphosphate carboxylase genes, the small subunit chlorophyll AB binding polypeptide, the 35S promoter of cauliflower mosaic virus, and promoters isolated from plant genes, including the Pto promoter itself (See Vallejos, et al., "Localization in the Tomato Genome of DNA Restriction Fragments Containing Sequences Homologous to the rRNA (45S), the major chlorophyll AJB Binding Polypeptide and the Ribulose Bisphosphate Carboxylase Genes," Genetics 112: 93-105 (1986) (disclosing the small subunit materials), which is hereby incorporated by reference in its entirety). The nos promoter and the 35S promoter of cauliflower mosaic virus are well known in the art.

In addition, the constructed DNA molecule may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," Proc. Nat'l. Acad. Sci. USA, 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," Nature, 313(6005):810-812 (1985), which is hereby incorporated by reference in its entirety). Virtually any 3' regulatory region known to be operable in plants would suffice for proper expression of the coding sequence of the constructed DNA molecule of the present invention.

Another type of regulatory sequence is known as an enhancer. Enhancer elements do not need to be located immediately upstream of the promoter or the sequence which encodes the transcript that will be made. Enhancers can, in fact, be located very far away. Nevertheless, they can also serve as regulatory elements, and could potentially be regulated by signaling molecules and thereby influence the expression of a target RNA inside a cell. Exemplary enhancer elements include, without limitation, the well-known SV40 enhancer region and the 35S enhancer element.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule that can be translated into the molecular complex of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus. Suitable vectors include, but are not limited to, the following viral vectors such as lambda vector system gtl 1, gt WES.tB, Charon 4, and plasmid vectors such as pBR322, pBR325, pACYCl 77, pACYC184, pUC8, pUC9, pUC18, pUC19, pLG339, pR290, pKC37, pKCIOl, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," Gene Expression Technology, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," Gene 151:209-214 (1994), which is hereby incorporated by reference in its entirety), p426GPD (see Mumberg et al., "Yeast Vectors for the Controlled Expression of Heterologous Proteins in Different Genetic Background," Gene 156:119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," Nucl. Acids Res. 22:5767-5768 (1994), which is hereby incorporated by reference in its entirety), pUAST (see Brand and Perrimon, "Targeted Gene Expression as a Means of Altering Cell Fates and Generating Dominant Phenotypes," Development 118:401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retroviral vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecule has been cloned into an expression system, it is ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., Molecular Cloning: A Laboratory Manual, Cold Springs Laboratory, Cold Springs Harbor, New York (1982), which is hereby incorporated by reference in its entirety. Suitable host cells include, but are not limited to, bacteria, yeast, mammalian cells, insect cells, plant cells, and the like. The host cell is preferably present either in a cell culture (ex vivo) or in a whole living organism (in vivo).

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-I cells, embryonic stem cells, induced pluripotent stem cells, and primary cells recovered directly from a mammalian organism. With regard to primary cells recovered from a mammalian organism, these cells can optionally be reintroduced into the mammal from which they were harvested or into other animals.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," Proc. Natl. Acad. Sci. USA 94:6676-6681 (1997); Shi et al., "RNA Aptamers as Effective Protein Antagonists In a Multicellular Organism," Proc. Natl. Acad. Sci. USA 96:10033-10038 (1999); Thomas et al., "Selective Targeting and Inhibition of Yeast RNA Polymerase II by RNA Aptamers," J Biol. Chem. 272: 27980-27986 (1997), which are hereby incorporated by reference in their entirety). Aptamer function within the nucleus of mammalian cells has also been demonstrated (Symensma et al., "Polyvalent Rev Decoys Act as Artificial Rev-Responsive Elements," J Viral. 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-I," Nucl. Acids Res. 30:4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," Proc. Natl. Acad. Sci. USA 101:11221-11226 (2004), which is hereby incorporated by reference in its entirety). Finally, most recently, very high levels of aptamer expression ($1 \times 10^7$ molecules per cell) have been achieved by fusion with a highly stable transcript (Choi et al., "Intracellular Expression of the T-cell Factor-I RNA Aptamer as an Intramer," Mal. Cancer Ther. 5:2428-2434 (2006), which is hereby incorporated by reference in its entirety).

Plant tissues suitable for transformation include leaf tissue, root tissue, meristems, zygotic and somatic embryos, and anthers. It is particularly preferred to utilize embryos obtained from anther cultures. The expression system of the present invention can be used to transform virtually any plant tissue under suitable conditions, and the transformed cells can be regenerated into whole plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety. Another method of introducing DNA molecules into a host cell is fusion of protoplasts with other entities, either minicells, cells, lysosomes, or other fusible lipid-surfaced bodies that contain the DNA molecule (Fraley et al., "Expression of Bacterial Genes in Plant Cells," Proc. Natl. Acad. Sci. USA 80:4803-4807 (1983), which is hereby incorporated by reference in its entirety). The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," Proc. Natl. Acad. Sci. USA 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," Mal. Gen. Genetics 202:179-85 (1985), which is hereby incorporated by reference in its entirety). The genetic material may also be transferred into the plant cell using polyethylene glycol (Krens et al., "In Vitro Transformation of Plant Protoplasts with Ti-Plasmid DNA," Nature 296:72-74 (1982), which is hereby incorporated by reference in its entirety). Alternatively, genetic sequences can be introduced into appropriate plant cells by means of the Ti plasmid of *A. tumefaciens* or the Ri plasmid of *A. rhizogenes*, which is transmitted to plant cells on infection by *Agrobacterium* and is stably integrated into the plant genome (Schell, "Transgenic Plants as Tools to Study the Molecular Organization of Plant Genes," Science 237:1176-83 (1987), which is hereby incorporated by reference in its entirety). After transformation, the transformed plant cells must be regenerated, and this can be accomplished using well known techniques as described in Evans et al., Handbook of Plant Cell Cultures, Vol. 1, MacMillan Publishing Co., New York (1983); and Vasil (ed.), Cell Culture and Somatic Cell Genetics of Plants, Acad. Press, Orlando, Vol. I (1984) and Vol. III (1986), each of which is hereby incorporated by reference in its entirety.

Selection of Biosensors

As discussed above, biosensors are generally initially made using randomly generated sequences for both the linker domain and the target domain. Hence, they are initially made in pools of a mixture of different biosensors. Not all the biosensors in this initial pool will have the properties of a biosensor, namely a high affinity for both the fluorophore and the target ligand and undergo an allosteric shift which effects the fluorescence of the biosensor in the presence of the target ligand compared to the absence of the target ligand. Therefore, it is preferable for this initial pool must undergo enrichment selection to reduce the number of possible biosensors.

Any method of selection known in the art may be used to enrich for biosensors which undergoes a shift in florescence due to an allosteric shift after a target ligand binds to a target domain. For example, see U.S. application Ser. No. 14/235,227 (herein incorporated by reference in its entirety) which uses selection in order to enrich for biosensors which bind to both the target ligand and the fluorophore, and do not have cross binding to other fluorophores.

However, unlike in U.S. application Ser. No. 14/235,227 it has been surprisingly found that using alternating rounds of "positive selection" and "negative selection" reduces the number of rounds of selection. As used herein, the term "positive selection" means an enrichment step where the biosensor will bind to the fluorophore in the presence of the target ligand. As used herein, the term "negative selection" means an enrichment step that removes biosensors that bind the fluorophore in the absence of the target ligand.

To perform selection, the fluorophore is bound to a solid substrate. This solid substrate may be any substrate known in the art, including, but not limited to, agarose beads, glass slides, or magnetic beads. The biosensors are then introduced to the bound fluorophores with either the target ligand present or absent. For negative selection, the target ligand is omitted from the process, but for positive selection the target ligand is present. The mixture is incubated to allow time for allosteric binding, followed by washing. The elute resulting from negative selection contains biosensors which may bind the fluorophore only in the presence of the target ligand or may not have an affinity for the fluorophore, therefore some of the biosensors in the elute may be suitable biosensors. The bound biosensors bind to the fluorophore without the target ligand present and are therefore unsuitable as biosensors. The elute from the positive selection are the biosensors which will not bind to the fluorophore in the presence of the target ligand and are therefore unsuitable for a biosensor. The biosensors which bind the fluorophore in the presence of the target ligand and may be suitable as a biosensor, which can then be washed off the solid support. Therefore, the eluate of the negative selection and the bound biosensors in the positive selection may be suitable for use as a biosensor according to the disclosure.

Any combination of negative and positive selection may be performed. Preferably positive selection follows a round of negative selection to take advantage of the elute of a round of negative selection comprising of biosensors which may be suitable according to this disclosure. Preferably, about 10 or fewer, about 8 or fewer, about 6 or fewer, or about 4 or fewer total rounds of selection are performed. For example, a pool of potential biosensors would be put through a round of negative selection, followed by two alternating rounds of positive followed by negative selection. Following the rounds of enrichment selection, the resulting pool of biosensors may then be optionally sequenced and individual biosensors chosen.

Optionally, it has been surprisingly found that the number of rounds of selection may be minimized by comparing the changes in counts or fold changes between rounds of selection. For example, a pool of potential biosensors, $A_0$, may undergo a round of negative selection followed by a round of positive selection, pool $A_1$. Representative samples of $A_0$ and $A_1$ may then be sequenced and the counts of unique sequences (potential biosensors) normalized and compared. Biosensors may be selected that exhibit an increase in count from $A_0$ to $A_1$ or that have a high $A_1:A_0$ ratio as these may show allosteric fluorescence (see Example 2 and FIG. 7B).

Another optional selection method would be to split a pool of potential biosensors, $B_0$, into two equal molar pools, $B_{0a}$ and $B_{0b}$. $B_{0a}$ may then undergo negative selection, $B_{1a}$, and $B_{0b}$ may undergo positive selection, $B_{1b}$. Representative samples of $B_0$, and the eluate of $B_{1a}$, and $B_{1b}$ may then be sequenced and the fold change of $B_{1a}$ and $B_{1b}$ calculated based on $B_0$. Potential biosensors may then be selected based on the change in fold change, with some biosensors expected to dim in the presence of the target ligand while others would show allosteric fluorescence (see Example 2 and FIG. 7C).

Uses and Kits of the Biosensors

The compositions of the various embodiments may be used to bind to a target ligand in a sample. The sample may be environmental, such as a water or soil sample, or be isolated from a subject, such as a human or animal blood or tissue sample. One skilled in the art would know how to obtain their respective sample for use with a biosensor.

After the respective sample is obtained, a biosensor of the disclosure is introduced into the sample along with the fluorophore. The sample, biosensor, fluorophore mix is incubated to allow for binding to a target ligand to form a molecular complex of the biosensor with both the target ligand or ligands and the fluorophore. The fluorophore may then be excited by the appropriate wavelengths to allow for the amount of the target ligand to be qualified or quantified by measuring the difference in brightness of the biosensor in the sample to a control biosensor. The change in brightness may either be an increase in brightness due to allosteric fluorescence or a dimming in brightness when compared to a control sample.

An alternative to comparing signal to a control sample is to compare to a control reporter within the sample. A known quantity of the control reporter may be added across samples, allowing the comparison of signal from one sample to another.

In another embodiment, the method further includes fixing a sample prior to introducing the biosensor and reporter into the sample. This may be done in to locate the position of a target within a sample, such as, but not limited to, subcellular structures, RNA, or cells, such as bacteria cells within an environmental sample.

Molecular Complexes

As discussed above, the biosensors may form molecular complexes with the target ligand and the fluorophore if both are present within a sample. These molecular complexes can exist in vitro, in isolated form, or in vivo following introduction of the biosensor (or a genetic construction or expression system encoding the same) into a sample, such as, but not limited to, a host cell or isolated environment or subject sample.

The molecular complex, therefore, can include the biosensor, one or more target ligands (bound specifically by the target domain(s)), and the fluorophore which is bound to the reporter domain These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes a plurality of target domain concatamers, each monomer including a target domain. The molecular complex, therefore, can include the biosensor, a plurality of target molecules (bound specifically by the plurality of target domains), and a fluorophore that is bound to the reporter domain. These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes target domain linked to a hybridization probe sequence that is complementary to a target domain. The molecular complex, therefore, can include the biosensor hybridized to the target nucleic acid molecule, and a fluorophore bound specifically to the reporter domain. These molecular complexes can exist in vitro, in isolated form or tethered to a substrate such as on an arrayed surface, or in vivo following introduction of the nucleic acid molecule (or a genetic construction or expression system encoding the same) into a host cell. In certain embodiments, these complexes can exist in fixed cells or on histologic tissue sections in the manner of an in situ hybridization protocol.

Specific examples of these types of molecular complexes, formed in vitro and in vivo, are disclosed in the accompanying Examples. It should be appreciated to skilled artisans that the host cells can be present in a whole organism, preferably a non-human organism.

For formation of the molecular complex inside a cell, the fluorophore is introduced into the cell where it can interact with (and be bound by) the receptor domain. According to one approach, the cell or the sample is contacted with the fluorophore by incubating the cell or the sample with the fluorophore. The fluorophore will be taken up by the cell, where it may freely diffuse throughout the cell. According to another approach, the fluorophore is injected into the cell or administered to a plant, embryo, mammal, or transgenic animal including the cell.

In the various methods of use, the formation of molecular complexes of the invention (e.g., fluorophore:biosensor:target complexes) can be identified, quantified, and monitored for various purposes, as discussed more fully below. Detection of molecular complex formation, through the fluorescent output of the fluorophore or a FRET partner (e.g., donor or acceptor), can be used to detect complex formation in a cell-free sample (e.g., cell extracts, fractions of cell extracts, or cell lysates), histological or fixed samples, tissues or tissue extracts, bodily fluids, serum, blood and blood products, environmental samples, or in whole cells. Thus, detection and quantification can be carried out in vivo by fluorescence microscopy or the like, or detection and quantification can be carried in vitro on any of the above extracts or on a sample obtained via in vitro mixing of sample materials and reagents.

The genetic constructs can be introduced into living cells using infective or non-infective transformation procedures that are well known in the art.

Regardless of the intended use, a suitable radiation source is used to illuminate the fluorophore after exposing the fluorophore and aptamer to one another. The radiation source can be used alone or with optical fibers and any optical waveguide to illuminate the sample. Suitable radiation sources include, without limitation, filtered, wide-spectrum light sources (e.g., tungsten, or xenon arc), laser light sources, such as gas lasers, solid state crystal lasers, semiconductor diode lasers (including multiple quantum well, distributed feedback, and vertical cavity surface emitting lasers), dye lasers, metallic vapor lasers, free electron lasers, and lasers using any other substance as a gain medium. Common gas lasers include Argon-ion, Krypton-ion, and mixed gas (e.g., Ar Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 mn. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 mm. Infrared radiation sources can also be employed.

Excitation wavelengths and emission detection wavelengths will vary depending on both the fluorophore and the nucleic acid aptamer molecule that are being employed. For example, thiazole orange has an excitation of 512 nm and an emission of 533 nm.

Detection of the emission spectra can be achieved using any suitable detection system. Exemplary detection systems include, without limitation, a cooled CCD camera, a cooled intensified CCD camera, a single-photon-counting detector (e.g., PMT or APD), dual-photon counting detector, spectrometer, fluorescence activated cell sorting (FACS) systems, fluorescence plate readers, fluorescence resonance energy transfer, and other methods that detect photons released upon fluorescence or other resonance energy transfer excitation of molecules.

In one embodiment, the detector is optically coupled to receive the output emissions of the fluorophore:biosensor: target complex through a lens system, such as in an optical microscope. In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In one embodiment, the interior surface of a glass or plastic capillary tube provides the substrate for the attachment of the fluorophore or the biosensor or a fluorophore: biosensor. The capillary can be either circular or rectangular in cross-section, and of any dimension. The capillary section containing the biosensors can be integrated into a microfluidic liquid-handling system which can inject different wash, buffer, and analyte-containing solutions through the sensor tube. Spatial encoding of the fluorophore or nucleic acid sensor molecules can be accomplished by patterning them longitudinally along the axis of the tube, as well as radially, around the circumference of the tube interior. Excitation can be accomplished by coupling a laser source (e.g., using a shaped output beam, such as from a VCSEL) into the glass or plastic layer forming the capillary tube. The coupled excitation light will undergo TIR at the interior surface/ solution interface of the tube, thus selectively exciting fluorescently labeled biosensors attached to the tube walls, but not the bulk solution. In one embodiment, detection can be accomplished using a lens-coupled, or proximity-coupled large area segmented (pixelated) detector, such as a CCD. In a particular embodiment, a scanning (i.e., longitudinal/axial and azimuthal) microscope objective lens/emission filter combination is used to image the biosensor substrate onto a CCD detector. In a different embodiment, a high resolution CCD detector with an emission filter in front of it is placed in extremely close proximity to the capillary to allow direct imaging of the fluorophore:nucleic acid aptamer complexes. In a different embodiment, highly efficient detection is accomplished using a mirrored tubular cavity that is elliptical in cross-section. The sensor tube is placed along one focal axis of the cavity, while a side-window PMT is placed along the other focal axis with an emission filter in front of it. Any light emitted from the biosensor tube in any direction will be collected by the cavity and focused onto the window of the PMT.

In still another embodiment, the optical properties of a biosensor are analyzed using a spectrometer (e.g., such as a luminescence spectrometer). The spectrometer can perform wavelength discrimination for excitation and detection using either monochromators (i.e., diffraction gratings), or wavelength bandpass filters. In this embodiment, the fluorophores of the molecular complexes are excited at absorption maxima appropriate to the fluorophore being used and fluorescence intensity is measured at emission wavelengths appropriate for the complexes being detected. Given that the intensity of the excitation light is much greater than that of the emitted fluorescence, even a small fraction of the excitation light being detected or amplified by the detection system will obscure a weak biosensor fluorescence emission signal. In one embodiment, the biosensor molecules are in solution and are pipetted (either manually or robotically) into a cuvette or a well in a microtiter plate within the spectrometer. In a further embodiment, the spectrometer is a multifunction plate reader capable of detecting optical changes in fluorescence or luminescence intensity (atone or more wavelengths), time-resolved fluorescence, fluorescence polarization (FP), absorbance (epi and transmitted), etc., such as the Fusion multifunction plate reader system (Packard Biosciences, Meriden, Conn.). Such a system can be used to detect optical changes in biosensors either in solution, bound to the surface of microwells in plates, or immobilized on the surface of solid substrate (e.g., a microarray on a glass substrate). This type of multiplate/ multisubstrate detection system, coupled with robotic liquid handling and sample manipulation, is particularly amenable to high-throughput, low-volume assay formats.

In embodiments where the sensor molecules or fluorophores are attached to substrates, such as a glass slide or in microarray format, it is desirable to reject any stray or background light in order to permit the detection of low intensity fluorescence signals. In one embodiment, a small sample volume (about 10 nl) is probed to obtain spatial discrimination by using an appropriate optical configuration, such as evanescent excitation or confocal imaging. Furthermore, background light can be minimized by the use of narrow-bandpass wavelength filters between the sample and the detector and by using opaque shielding to remove any ambient light from the measurement system.

In one embodiment, spatial discrimination of a molecular complex of the invention (fluorophore:nucleic acid aptamer complexes or fluorophore:nucleic acid aptamer:target molecule complexes) attached to a substrate in a direction normal to the interface of the substrate is obtained by evanescent wave excitation. This is illustrated in PCT Application Publ. No. WO/2010/096584 to Jaffrey and Paige, which is hereby incorporated by reference in its entirety. Evanescent wave excitation utilizes electromagnetic energy that propagates into the lower-index of refraction medium when an electromagnetic wave is totally internally reflected at the interface between higher and lower-refractive index materials. In this embodiment a collimated laser beam is incident on the substrate/solution interface (at which the fluorophore:biosensor complexes or fluorophore:biosensor: target molecule complexes are immobilized) at an angle greater than the critical angle for total internal reflection (TIR). This can be accomplished by directing light into a suitably shaped prism or an optical fiber. In the case of a prism, the substrate is optically coupled (via index-matching fluid) to the upper surface of the prism, such that TIR occurs at the substrate/solution interface on which the molecular complexes are immobilized. Using this method, excitation can be localized to within a few hundred nanometers of the substrate/solution interface, thus eliminating autofluorescence background from the bulk analyte solution, optics, or substrate. Target recognition is detected by a change in the fluorescent emission of the molecular complex, whether a change in intensity or polarization. Spatial discrimination in the plane of the interface (i.e., laterally) is achieved by the optical system.

In the embodiment described above, a TIRF evanescent wave excitation optical configuration is implemented using a detection system that includes a universal fluorescence microscope. Any fluorescent microscope compatible with TIRF can be employed. The TIRF excitation light or laser can be set at either an angle above the sample shining down on the sample, or at an angle through the objective shining up at the sample. Effective results can been obtained with immobilization of either the aptamer or the fluorophore using NETS-activated glass slides. The fluorophore containing a free amine (at the R1 position) can be used to react with the NETS-slide. RNA can be modified with a 5' amine for NETS reactions by carrying out T7 synthesis in the presence of an amine modified GTP analog (commercially available).

In the several embodiments described above, the output of the detection system is preferably coupled to a processor for processing optical signals detected by the detector. The processor can be in the form of personal computer, which contains an input/output (I/O) card coupled through a data bus into the processor. CPU/processor receives and processes the digital output signal and can be coupled to a memory for storage of detected output signals. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a software package (for image processing) for carrying out one or more aspects of the present invention as described herein.

In addition to their specificity in binding to fluorophores, a number of the aptamers have demonstrated that their affinity for the target fluorophore can be modulated by environmental conditions.

In another aspect of the disclosure, an embodiment comprises a kit which may be used to binding a desired target in a sample. The kit may comprise of the biosensor and/or a nucleic acid comprising the biosensor and additional functional regions, such as, but not limited to, one or more promoter regions. In additional embodiments, the kit may further comprise of the reporter molecule, by way of non-limiting example TOB1; reference dye; buffers; solvents, such as but not limited to polar or organic solvents; and/or instructions.

The disclosure is further illustrated by the following example which should not be construed as limiting. The examples are illustrative only, and are not intended to limit, in any manner, any of the aspects described herein. The following examples do not in any way limit the invention.

EXAMPLES

Example 1

RNA aptamers that bind fluorogenic ligands are emerging as useful tools for basic and applied biology. However, it is unknown how adding additional functional groups will affect the Mango cores affinity to or the brightness of a fluorophore. It has been shown previously that the aptamer can maintain fluorescence and ligand affinity when the stem is relocated to any of the corners of the quadruplex. Based on the results of this previously reported stem permutation experiment, combined with the multi-helical structure of other fluorogenic aptamers, it may be possible to design two-stemmed variants of Mango cores that maintain fluorescence and provide more design possibilities. We note that the binding of TO1-biotin to the RNA Mango-I aptamer includes interactions between the G bases at the face of the G-quadruplex and interactions with nucleobases from the loops of the quadruplex. Specifically, the heterocyclic ring of TO1-Biotin is stacked above by two adenosine residues and the biotin moiety interacts with the base surface of a uracil. These "A/U flaps" were highly conserved in molecules selected to bind TO1-biotin and are necessary for fluorescence. This is important because any two-stemmed designs must not only enable proper quadruplex formation but must also allow these nucleotide flaps to interact favorably with the ligand.

Figure 1B:
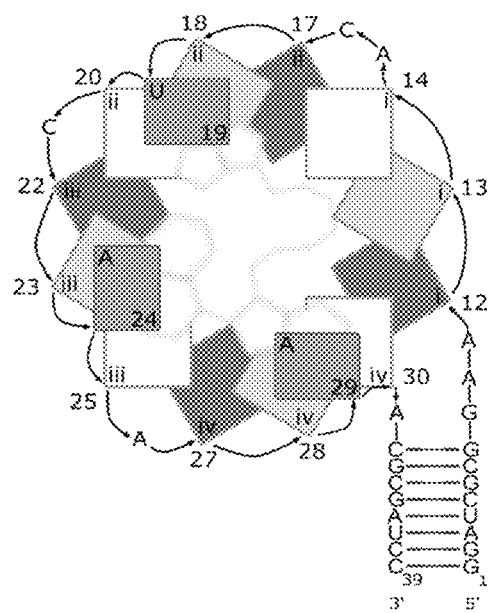
FIG. 1B is a schematic representation of an exemplary Mango I aptamer bound to TO1-biotin with individual nucleotides numbered 1-39 and edge nucleotides labeled with their edge designation as set out in FIG. 1A. Rectangles along the edges are guanine residues (SEQ ID NO: 2).

To test RNA Mango-I variants that have two base-paired stems attached to the G-quadruplex, the Mango-I aptamer was redesigned based off the crystal structure of Mango-I. Looking at this structure with the ligand-binding face of the G-quadruplex toward you, the structure appears square-like. Each edge of the square comprised of three G residues that each contribute to one tier of the quadruplex (FIG. 1A). To facilitate the design process, we have created an abstract representation of the structure (FIG. 1B). The Mango aptamer also requires that the stem is connected to the corner of the quadruplex with a four-nucleotide bulge region that is referred to as a tetraloop-like motif Material and Methods RNA Transcription and Purification Mango variants were made by in vitro transcription from synthetic oligonucleotide templates (IDT). The T7 promoter regions of each template were made double stranded by annealing a second oligonucleotide with the sequence of the top strand of the promoter. DNA was heated to 95° C. for 5 min and cooled to room temperature in 1×T7 buffer. This primer-annealed template was added to a transcription reaction containing 15 mM ribonucleotide triphosphate mix (NEB: N0466S), 5 mM DTT, 2 mM Spermidine, 3 mM Tris pH 7.5, and ~800 units of T7 RNA polymerase (Thermo Fisher Scientific: EP0113). RNA was purified on a 12% polyacrylamide gel with 8M urea. Bands were visualized with a brief exposure to UV light, and excised with sterile razor blades. Gel was crushed and eluted in 300 mM sodium acetate (RNase Free) at room temperature for one hour. The crushed gel samples were passed through a 0.2 μm sterile filter by centrifugation and ethanol precipitated with 3 volumes of 95% cold ethanol at −20 C for 5 minutes. RNA was pelleted by centrifugation at 4° C. for 20 minutes and washed with 80% then 95% ethanol. Pellets were dried in a SpeedVac for approximately two minutes then rehydrated in RNase free water and quantified by A260 (NanoDrop). Purified RNA was run again on an analytical 12% denaturing polyacrylamide gel for quality control.

Characterization of Binding Affinity and Maximum Fluorescence

Serial RNA dilutions were made using a 1× Mango Buffer which contains 1 mM MgCl2, 10 mM $NaH_2PO_4$ (pH 7.4), and 140 mM KCl. Relative fluorescence was measured with a DeNovix QFX fluorometer. Best fit curves were generated using a non-linear regression function from the Scipy_Optimize package in python. The averages of the triplicate data were fit using a Trust Region Reflective least squares algorithm to Eq. 1 where [apt] and [TO1-B] are the concentrations of Mango and TO1-Biotin in nM, respectively. F' is the molar maximum fluorescence which is the $F_{max}/[TO1\text{-}B]$. The 95% confidence intervals were calculated using the python uncertainties package.

$$F([apt]) = \frac{F'\left[(K_D + [apt] + [TO1 - B]) - \sqrt{(([apt] - [TO1 - B])^2 + K_D(K_D + 2[apt] + 2[TO1 - B]))}\right]}{2} \quad \text{Eq. 1}$$

Split RNA Preparation

Split RNA aptamers were synthesized and purified as described above as individual strands. The purified split RNA aptamer strands were mixed in 1× Mango buffer at the appropriate concentrations. The samples were then incubated at 65 C for 2 minutes and cooled to room temperature for 5 minutes. Upon completion of the room temperature incubation, the samples were serially diluted tested for fluorescence.

Kinexa Fluorescent Measurement Assays

The dissociation constant was measured by affinity exclusion assay with a KinExA model 3200 (Sapidyne, Boise, ID). Five-fold dilutions of TO1-3PEG-biotin (Applied Biological Materials, Vancouver, BC), beginning with 1.0 μM, were prepared each with 5.0 nM RNA in 1× Mango buffer. Samples were also supplemented with 0.02% tween-20 to minimize non-specific binding to the KinExA tubing system. Samples were allowed to equilibrate for four hours at room temperature. The stationary phase of the system consisted of polymethylmethacrylate beads coated with BSA-biotin (Sigma), followed by avadin (MP Biomedicals) and TO1-3PEG-biotin in accordance with Sapidyne protocols. Following introduction of the sample, buffer was flowed across the flow cell for seven minutes. Free aptamer from each equilibrium mixture bound to the TO1B affixed to the beads and the resulting fluorescence was measured. $K_D$ was calculated by the KinExA software using the equilibrium protocol.

Results and Discussion

Design of Second Stem Composition, Length, and Position

To facilitate proper folding of Mango constructs, w two different stems with unique base compositions were designed. For the first stem the 8 bp stem that was reported with the original selection of RNA Mango was used. A second 8 bp stem was designed with sequence composition that was not expected to form substantial base pairs with either the first stem or the bases of the G-quadruplex (see FIGS. 2A-2F). Several sequences were designed and tested using thermodynamic structure prediction (Nupack). The second stem shown in FIGS. 2A-2F was chosen because it formed the expected base pairs in the two stems with very low probability of other base pair interactions (data not shown).

Six unique Mango constructs were designed by joining the two stems to different corners of the G-quadruplex (FIGS. 2A-2D). These designs are designated by the corners where each stem was joined to the quadruplex. For example, Mango i-iv ii-i has the closing stem connected at the i-iv corner with the second stem in the ii-i corner. The closing stem and the second stem each replace at least one nucleotide in the loops when inserted into the G-quadruplex. A single adenosine residue in was inserted into corner i-iv for designs that did not have a stem at this corner. Our designs used the GAAA tetraloop-like linker in the same orientation for both stems.

Relative $F_{max}$ and Closing Stems Groups

Figure 5A:
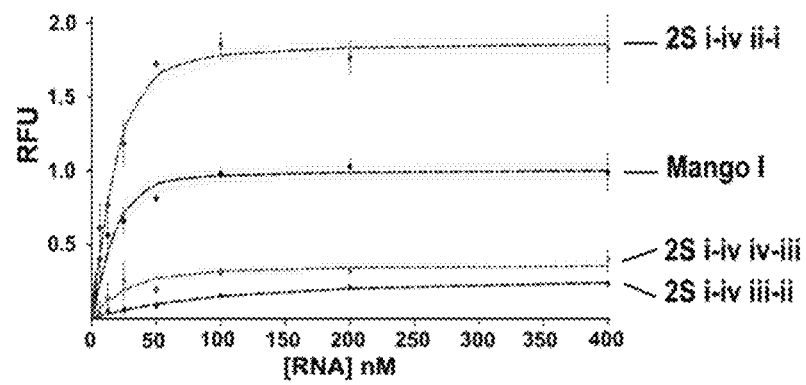
FIG. 5A is a graphical representation of the fluorescence saturation curve of the two-stemmed Mango variants with 25 nM TO1-B and variable RNA concentrations. Shaded regions show 95% C.I. of the curve fit with the second closed stem at the i-iv corner (see FIGS. 2A-2C for schematic representations).
Figure 5B:
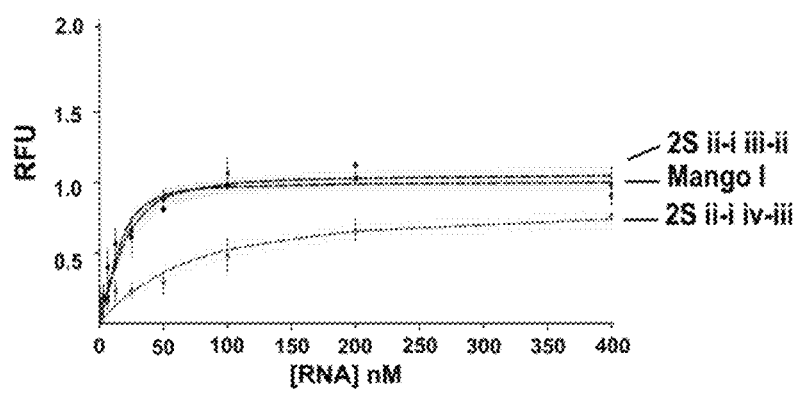
FIG. 5B is a graphical representation of the fluorescence saturation curve of the two-stemmed Mango variants with 25 nM TO1-B and variable RNA concentrations. Shaded regions show 95% C.I. of the curve fit with the second closed stem at the ii-i corner (see FIGS. 2D-2E for schematic representations).
Figure 5C:
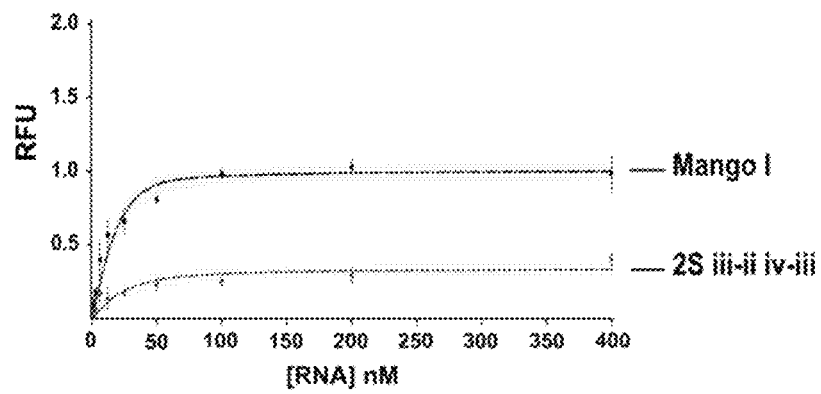
FIG. 5C is a graphical representation of the fluorescence saturation curve of the two-stemmed Mango variants with 25 nM TO1-B and variable RNA concentrations. Shaded regions show 95% C.I. of the curve fit with the second closed stem at the iii-ii corner (see FIG. 2F for schematic representations).
Figure 5D:
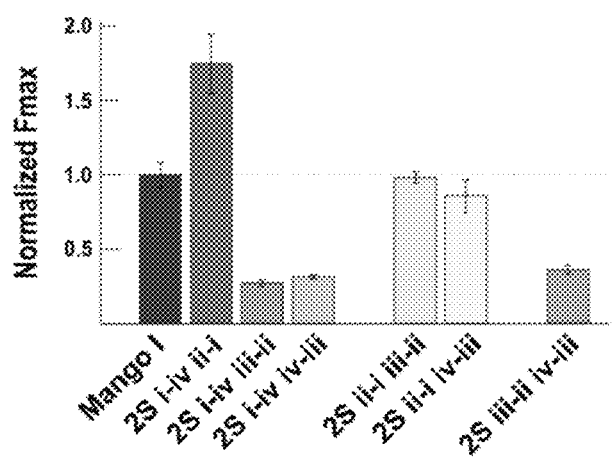
FIG. 5D is a graphical representation of the relative maximum fluorescence ($F_{max}$) of the two-stemmed variants.
Figure 5E:
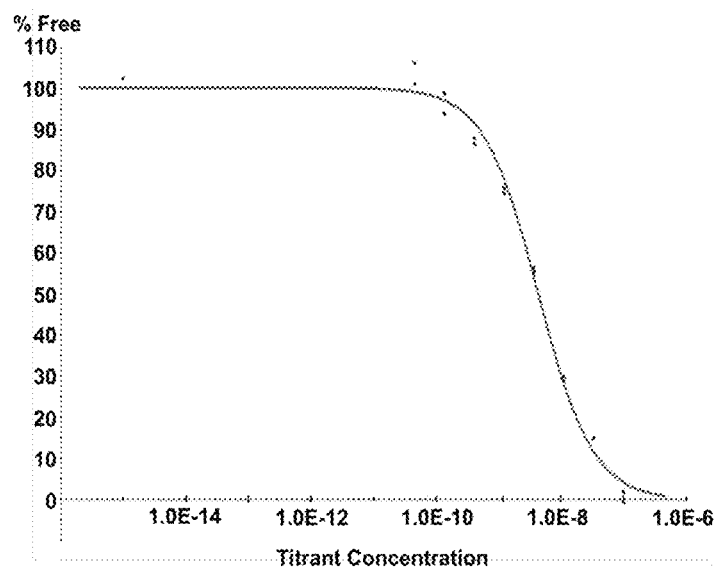
FIG. 5E is a graphical representation of the fraction of Mango i-iv ii-i in free solution over a range of TO1-B concentrations.
Figure 5F:
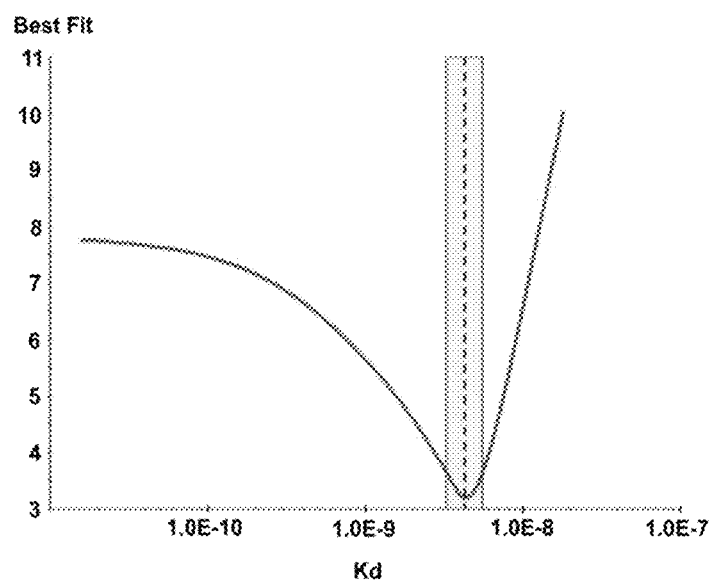
FIG. 5F is a graphical representation of the Best fit KD curve with 95% C.I. (shaded).

To evaluate the fluorescence and ligand affinity of the six Mango variants, we measured the fluorescence at various concentrations of RNA, with a fixed TO1-B concentration of 25 nM. Non-linear curve fitting was used to determine $F_{max}$ and $K_d$. The single-stem Mango-I was measured and reported $F_{max}$ values as relative to this construct (FIGS. 5A-5C). Not surprisingly, three variants had very low ligand affinity and poor fluorescence. However, it was found that two of the variants had maximum fluorescence values as bright or brighter than the original single-stem Mango I. In addition, the two variants had $K_d$ values in the low nanomolar range. The brightest two-stemmed construct was Mango i-iv ii-i, which was 75% brighter than the single-stem Mango-I ($F_{max}$=1.75±0.08). The binding affinity for this brightest Mango i-iv design was confirmed using a KinExA binding affinity assay, which measured a $K_d$ of 4.35 nM (95% C.I. of 3.28-5.57 nM) (FIGS. 5E-5F). This two-stemmed construct and the original Mango-I share the same closing stem connection point at corner i-iv. The second brightest two-stemmed construct Mango ii-i iii-ii used a different closing corner, but still showed a fluorescence saturation curve nearly identical to Mango-I ($F_{max}$=0.98±0.04), indicating that the i-iv corner is not a requirement for two-stemmed designs (FIG. 5B). Our third brightest construct Mango ii-i iv-iii, was not quite as bright as the original single-stemmed Mango-I ($F_{max}$=0.86±0.11), and this design showed reduced ligand affinity (FIG. 5B, lower curve).

Relationship Between Stems, Flaps, and Fluorescence

Comparing the structural differences of the two-stemmed variants might lead to better design rules for future designs. From a topological perspective, surprisingly the constructs with the highest maximum fluorescence all use corner ii-i. Interestingly, this is the only corner of the quadruplex that does not contain an A/U flap nucleotide. The constructs that showed very low fluorescence had both stems joined to a corner that contained an A/U flap nucleotide. Since each individual placement was shown to maintain fluorescence and affinity, it is believed, without being bound by any particular theory, that ligand binding is compromised by the combined effect of having two stems located at corners adjacent to A/U flaps. This is further indicated by the three constructs that use the i-iv corner for the closing stem (FIG. 5A). High $F_{max}$ was only observed when the second stem was placed at the ii-i corner ($F_{max}$=1.75). Another possibility is that the specific RNA sequences that show low $F_{max}$ all misfold a significant fraction of the time, forming structures that do not bind or stabilize the ligand. If this is true, it might be possible to find brighter versions of all designs by altering either the base composition of the stem or by changing the length or composition of the tetraloop-like linker.

Without being bound by any particular theory, there may be several possibilities of why the Mango i-iv iii-ii construct produces higher maximum fluorescence than the Mango I. One possibility is that the presence of a second stem may add structural stability, resulting in a greater fraction of correctly folded RNA molecules. While this is possible, the Mango ii-i iii-ii construct should also have the added stability of the second stem, but this construct had a maximum fluorescence that was the same as Mango I. This suggests that second stem stability alone is not enough to improve fluorescence. Another possibility is that the second stem creates better fluorescence enhancement of the ligand once bound. This could be accomplished if the added sequence creates specific tertiary interactions between the second stem and the quadruplex core. This is observed, for example, in the structure reported for the variant referred to as Mango-III, which also shows brighter maximum fluorescence than Mango-I. Mango-III achieves this through a pseudoknot-like tertiary interaction. Another possibility is that the second stem of the Mango i-iv iii-ii construct interacts directly and favorably with the TO-1 biotin.

Demonstration of Split RNA Mango

Figure 2A:
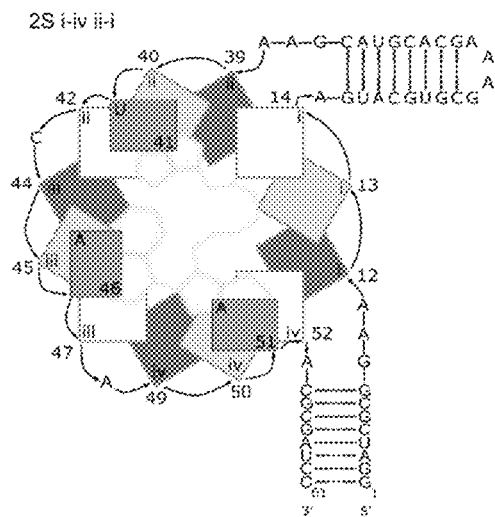
FIG. 2A is a schematic representation of an exemplary Mango I aptamer bound to TO1-biotin with a i-iv open stem and an ii-i closed stem with individual nucleotides numbered and edge nucleotides labeled with their edge designation as set out in FIG. 1A. Rectangles along the edges are guanine residues (SEQ ID NO: 3).
Figure 2B:
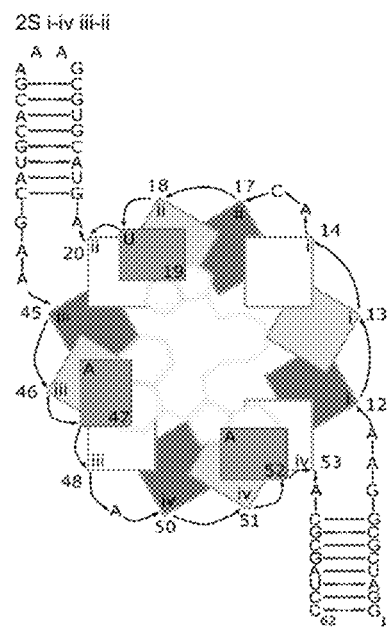
FIG. 2B is a schematic representation of an exemplary Mango I aptamer bound to TO1-biotin with a i-iv open stem and an iii-ii closed stem with individual nucleotides numbered and edge nucleotides labeled with their edge designation as set out in FIG. 1A. Rectangles along the edges are guanine residues (SEQ ID NO: 4).
Figure 2C:
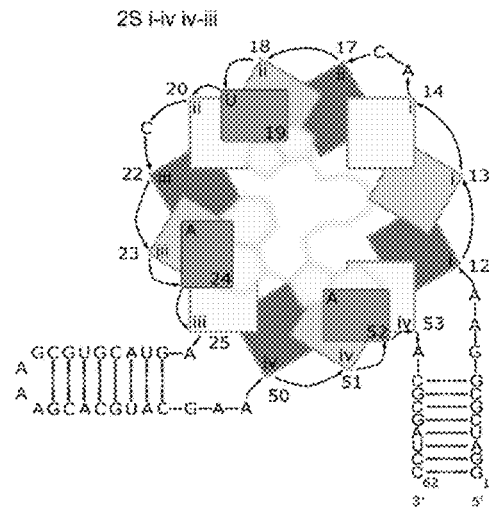
FIG. 2C is a schematic representation of an exemplary Mango I aptamer bound to TO1-biotin with a i-iv open stem and an iii-iv closed stem with individual nucleotides numbered and edge nucleotides labeled with their edge designation as set out in FIG. 1A. Rectangles along the edges are guanine residues (SEQ ID NO: 5).
Figure 2D:
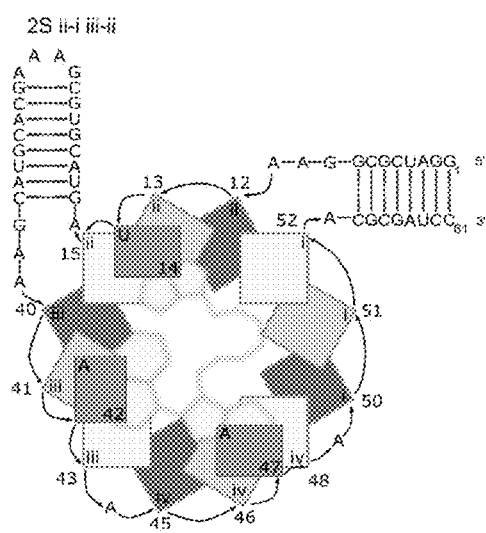
FIG. 2D is a schematic representation of an exemplary Mango I aptamer bound to TO1-biotin with a ii-i open stem and an iii-ii closed stem with individual nucleotides numbered and edge nucleotides labeled with their edge designation as set out in FIG. 1A. Rectangles along the edges are guanine residues (SEQ ID NO: 6).
Figure 2E:
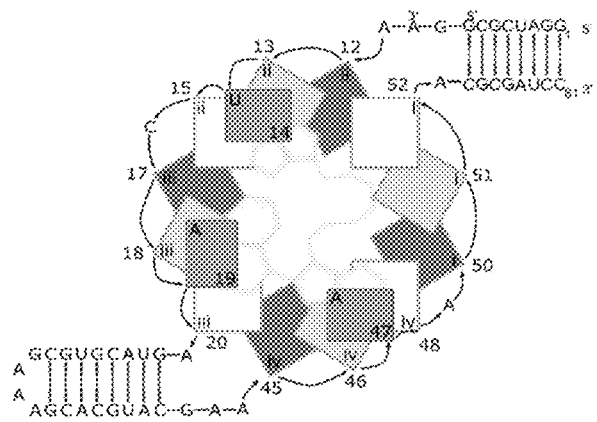
FIG. 2E is a schematic representation of an exemplary Mango I aptamer bound to TO1-biotin with a ii-i open stem and a iv-iii closed stem with individual nucleotides numbered and edge nucleotides labeled with their edge designation as set out in FIG. 1A. Rectangles along the edges are guanine residues (SEQ ID NO: 7).
Figure 2F:
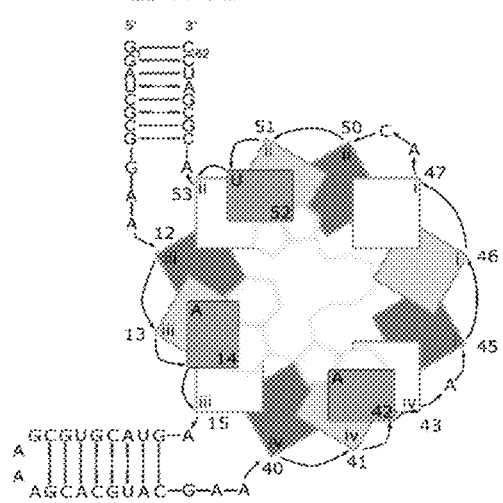
FIG. 2F is a schematic representation of an exemplary Mango I aptamer bound to TO1-biotin with a iii-ii open stem and a iv-iii closed stem with individual nucleotides numbered and edge nucleotides labeled with their edge designation as set out in FIG. 1A. Rectangles along the edges are guanine residues (SEQ ID NO: 8).
Figure 2G:
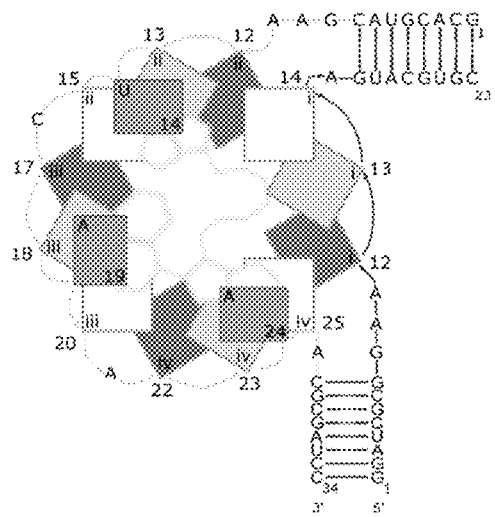
FIG. 2G is a schematic representation of an exemplary split Mango I aptamer bound to TO1-biotin with iv-i and ii-i open stems with individual nucleotides numbered and edge nucleotides labeled with their edge designation as set out in FIG. 1A. Rectangles along the edges are guanine residues (SEQ ID NOs: 9-10).
Figure 2H:
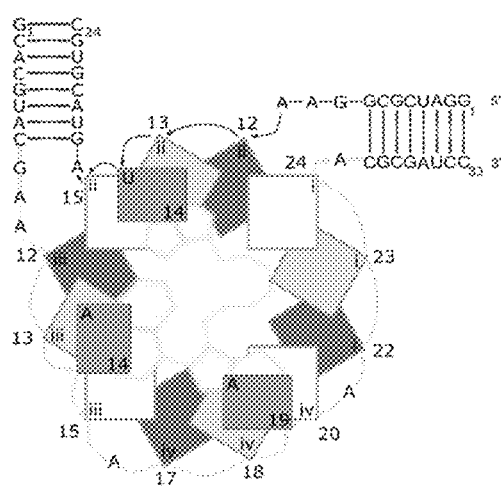
FIG. 2H is a schematic representation of an exemplary Mango I aptamer bound to TO1-biotin with ii-i and iii-ii open stems with individual nucleotides numbered and edge nucleotides labeled with their edge designation as set out in FIG. 1A. Rectangles along the edges are guanine residues (SEQ ID NOs: 11-12).
Figure 6A:
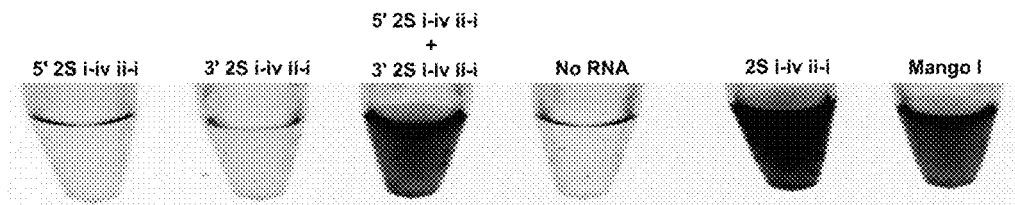
FIG. 6A is a photograph representation of the fluorescence of split Mango constructs showing the difference in fluorescence between the 5' Split Mango i-iv ii-i strand only, 3' Split Mango i-iv ii-i strand only, both strands of Split Mango i-iv ii-i, no RNA, Mango i-iv ii-i, and Mango I (see FIGS. 2G and 2H for graphical representations of split Mango).
Figure 6B:
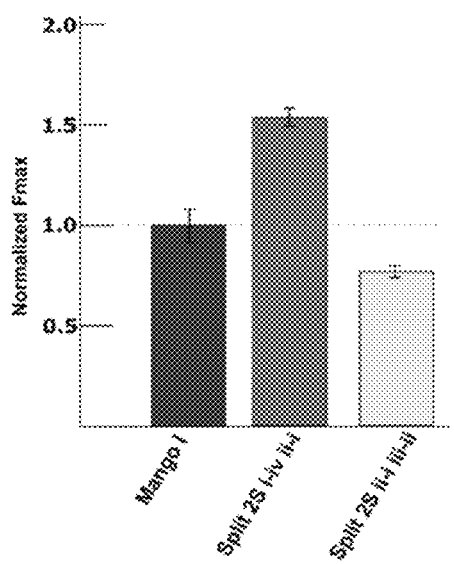
FIG. 6B is a graphical representation of the normalized $F_{max}$ of both split Mango i-iv-ii-i and split Mango ii-i iii-ii when compared to Mango-I in 40 nM TO1-B.

The high fluorescence of the two brightest constructs may enable fluorescent-enhancing ligand binding even when the aptamer is split into two or more separate RNA strands and reconstituted in a bi-molecular structure. To design the split constructs, the tetraloop was removed in the second stem to effectively break the structure into two separate RNA sequences. Each required RNA sequence was transcribed in separate in vitro transcriptions and then mixed them back together in the presence of TO1-biotin and Mango buffer to determine fluorescence (FIGS. 6A-6B). A simple visual appraisal in tubes confirmed fluorescence (FIGS. 2G-2H). A signal was achieved only when both RNA strands were present, and the individual single strands showed background fluorescence indistinguishable from TO1-Biotin alone ("No RNA" control). To further characterize the split constructs, the fluorescence while varying the concentration of the two halves of the construct was determined. Structure prediction (Nupack) indicated that a 2:1 ratio of one strand to the other would ensure that the majority of the lower concentration strand would be in bimolecular constructs. To determine if there was a difference in which strand needed to be in excess, various concentrations of one strand of RNA (0-800 nM) with the other strand held constant at 200 nM were mixed together (data not shown). Surprisingly, it was found that the strand that contains edge i is required to be in excess in by 2-fold to the other strand in order to reach a maximum fluorescence similar to the unimolecular two-stemmed construct. We measured the fluorescence at these various concentrations of total RNA with a fixed TO1-B concentration (40 nM) and again used non-linear curve fitting to determine $F_{max}$ and $K_D$. Interestingly, the split designs showed nearly identical $F_{max}$ as compared to the unimolecular two-stemmed constructs (FIG. 6B), indicating efficient folding of the bimolecular structures.

Conclusions

The two-stemmed RNA Mango constructs reported expand the designability of the fluorogenic Mango aptamers. It remains difficult to predict unwanted sequence interactions that might occur during different applications but having two different two-stemmed constructs that do not compromise ligand affinity or maximum fluorescence might be useful for challenging designs. In addition, the Mango i-iv ii-i two-stemmed construct that showed brighter maximum fluorescence than the original single-stemmed Mango-I may prove to be useful for in vivo applications. It was found that the A/U flaps that interact with TO1-biotin ligand appeared to limit the placement of multiple stems in this RNA aptamer. This highlights the challenges that remain for RNA structural prediction, especially when non-canonical structures such as G-quadruplexes are important for function.

RNA-RNA interactions are critical for numerous processes including spliceosomal assembly and function, RNA modification, RNA interference pathways, bacterial small RNA and CRISPR/Cas systems, among others. However, the study of RNA-RNA interactions remains challenging. Our split designs could be used to detect RNA-RNA interactions, for example, if one of the stems is replaced by parts of two separate RNA molecules that interact with appropriate affinity. Fine tuning of both stems will likely be required. In addition, the simple split designs reported here could function as a rapid fluorescence-based assay for RNA helicase activity. The split designs might also be useful in designing genetically encodable fret systems and other RNA origami applications.

Example 2

Biosensors must have the ability to detect target, transduce signal, and express signal. Some sensors require a dose-response analysis, and some require confirmation of the presence or absence of an analyte. In addition to these requirements, a biosensor that has the ability to be genetically encodable, utilize a fluorescent reporter, and have a simple workflow is desirable. While this disclosure can accommodate both the qualitative and quantitative reporting requirements of in vitro diagnostics (IVD), this example of a biosensor was limited to the presence or absence of the effector molecule Theophylline. There are numerous reports detailing which paradigm should be reported by diagnostics making it more important that the biosensors of the disclosure can do both. Biosensor were designed as a plug and play (PnP) platform that requires minimal selections to develop new and novel biosensors.

The PnP biosensor workflow is different from many in vitro diagnostic testing workflows, such as Enzyme-linked Immunosorbent Assay (ELISA). ELISA testing requires several wash and incubations steps during which much care must be taken to control the temperature, incubation times, and exposure to light. Any deviation during one of the critical steps, such as incomplete removal of a chromophore linked antibody, will yield false results. The biosensor design laid out by this process was designed to have no washing steps with only a single incubation step. The incubation step was designed to be compatible with prokaryotic and eukaryotic cell culture temperatures and may be altered in future protocols. Our simple workflow biosensor is a PnP design which is centered around modular domains each with a separate and distinct function.

Figure 3A:
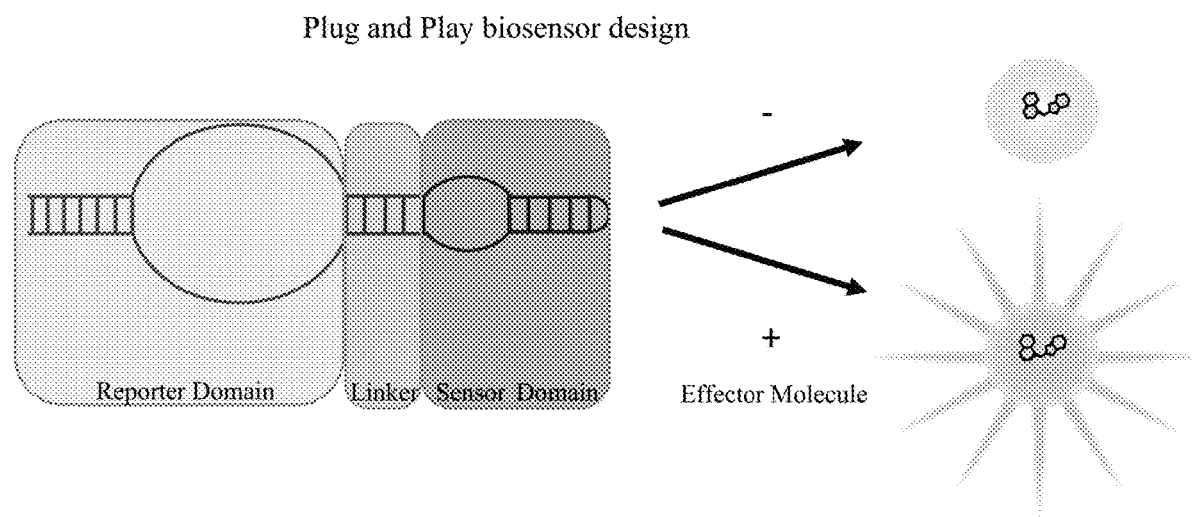
FIG. 3A is a schematic representation of the Mango core, linker, and a closed sensor domain showing the presence of the target ligand determining the final state of the fluorophore through allosteric fluorescence.
Figure 3B:
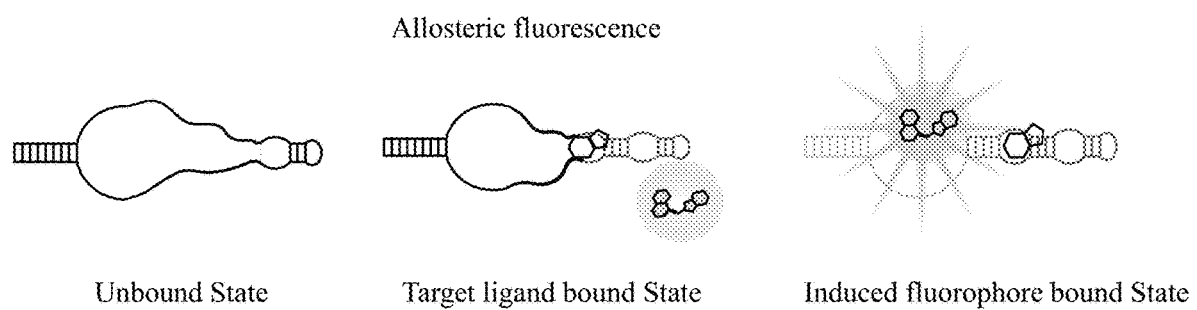
FIG. 3B is a schematic representation of the induction of fluorescence by a target ligand showing the unbound biosensor is stabilized by the target ligand, which in turn stabilizing the fluorophore binding pocket.

Sequence design was divided out into three separate domains (FIG. 3A). The reporter domain is based off the Mango platform and Example 1 above. The positions of the second stems are important, as shown above the location where additional aptamers may be inserted and still have the desired interaction between the G-quadruplex and the dye. The reporter domain is responsible for the emission of the signal, in this case fluorescence, which is one of the requirements for a biosensor. The sensor domain is responsible for target recognition which is comprised of a known aptamer that has been previously characterized. Signal transduction happens between the target domain and the reporter domain via the communication domain (linker or linker domain). As the target molecule is bound by the nucleic acid strand it induces a conformational change through the communication domain allowing the dye to be bound in the reporter domain. This allosteric mechanism is similar to a class of molecules called Ribozymes. This class of molecules utilize allosteric functions in nature and were an early target for ligand induced allosteric function (FIG. 3B).

Allosteric fluorescence is the induction of a fluorescent signal due to the binding of an effector molecule. The theophylline aptamer was chosen as an exemplar effector molecule because it is well characterized and has been used in other allosteric aptamers. However, any target domain may be substituted for the theophylline aptamer. The theophylline aptamer was previously discovered by the SELEX procedure and was highly discriminatory for theophylline over similar xanthines.

The addition of allosteric fluorescence to into a functional RNA aptamer sequence had already been accomplished with the RNA Spinach aptamer. RNA Spinach was the first fluorogenic aptamer to undergo the addition of allosteric fluorescence. Initially, aptamers that bound ADP, SAM, GTP, and adenosine were fused to the RNA Spinach aptamer. RNA Spinach has an advantage over RNA Mango when considering design and engineering. As stated earlier, RNA Mango I is comprised of a single closing stem which limits the ability to add additional structure. Unlike RNA Mango, RNA Spinach has two stems which is more conducive to allosteric engineering. The addition of a second stem allows engineers to add additional structure to the surrounding functional central core and was a motivation for our allosteric engineering work. The second stem makes engineering around a central highly conserved core easier and more likely to succeed. Example 1 above of engineering insertion points of additional structure into and around Mango's central core provides multiple design and engineering pathways to adding complex structures into the Mango G-quadruplex. However, early structural engineering of Mango I only included simple hairpins and did not include allosteric elements. To shows that allosteric fluorescence may be achieved with a Mango core, a known aptamer that has well established functionality was added in addition to a linker domain. Since Mango I has been shown to tolerate additional stems being coupled to the central core in Example 1, a biosensor with allosteric fluorescence was designed.

Engineering and Design Considerations

Figure 4A:
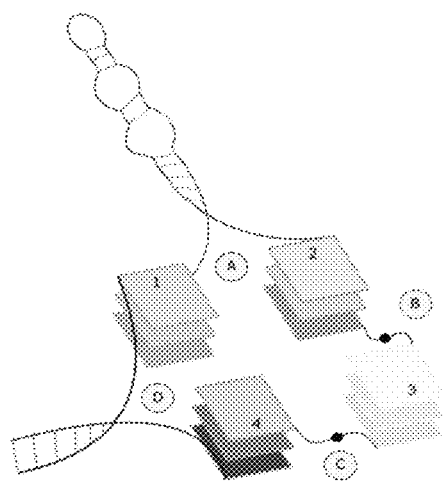
FIG. 4A is a simplified schematic representation of a Mango-Theophylline-N8 starting library with a closed stem in the i-iv position and a closed stem with the N8 linker and Theophylline sensor in the ii-i position, or further abbreviated A position (MTS14A).
Figure 4B:
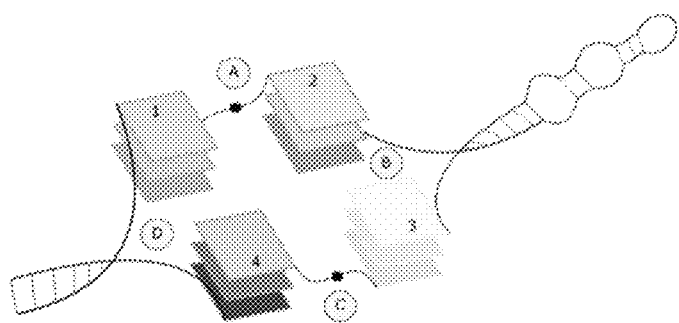
FIG. 4B is a simplified schematic representation of a Mango-Theophylline-N8 starting library with a closed stem in the i-iv position and a closed stem with the N8 linker and Theophylline sensor in the iii-ii position, or further abbreviated B position (MTS14B).
Figure 4C:
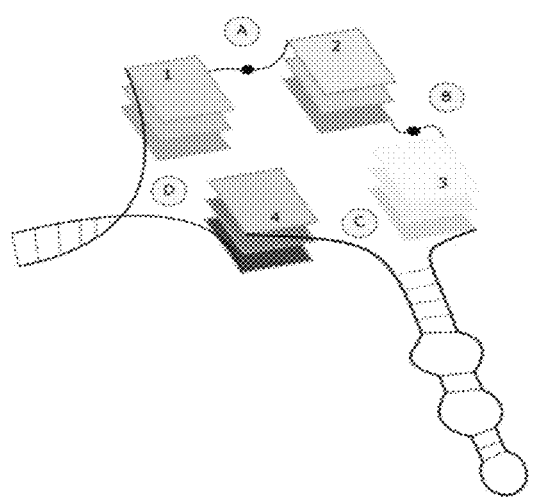
FIG. 4C is a simplified schematic representation of a Mango-Theophylline-N8 starting library with a closed stem in the i-iv position and a closed stem with the N8 linker and Theophylline sensor in the iv-iii position, or further abbreviated C position (MTS14C).

Even though Example 1 shows that additional stems are capable of being inserted, several unknowns still must be addressed when we designed initial libraries for the Mango-Theophylline Switch (MTS). We had several closing stem positions to consider as well as their corresponding second stem position. It was unknown which position would yield the best allosteric fluorescence or "switching effect" upon addition of theophylline. It was unknown which starting positions should be used, such as a relatively dim switch, position 14B, and try to increase fluorescence through the binding of theophylline or use a brighter position (14A) and try to increase fluorescence through better rigidification of the TO1B through theophylline binding (see FIGS. 4A-4C). The i-iv closing stem with all the second stem permutation anchor points for a total of three libraries was initially selected (FIG. 4A-4C). This closing stem series demonstrated a wide range of from fluorescence from the highly fluorescent 2S i-iv ii-i (14A) to the dim 2S i-iv (14B). Another unknown was how long to make the communication domain. It has been demonstrated that an 8-base paired stem will induce fluorescence of the Mango I central core. It is also known that the reducing the closing stem below 5 base pairs will significantly reduce fluorescence and that removing the stem will suppress the fluorescent ability of the Mango I central core. An intermediate linker length of 4 paired nucleotides (8 total nucleotides) was chosen, which is in the middle of always on (full fluorescence) and always off (minimal fluorescence). The 4-paired nucleotide communication domain was then randomized. The linker was then coupled to a truncated theophylline aptamer (the target domain) with a single base pair remaining on the end of the conserved theophylline binding pocket. This was done to partially destabilize the theophylline binding pocket without destroying the binding pocket ability. We omitted the necessary GAAA tetraloop-like motif as this sequence would be included in the some of the sequence space generated by our random libraries. Each library generates $4^8$ (65,563) unique sequences. Library size was 196,608 unique sequences when all three-equal molar Man-Theo N8 ($4^8$) libraries were combined. Another benefit of the N8 library is that it provides good coverage throughout the whole selection process. Each of or sequences will have approximately 3,000,000× coverage when initial rounds of selection are started.

A strategic pattern of round type was employed to manipulate our RNA selection pools. A negative selection round to deplete the non-functional sequences was used to start, which was estimated to abundant in the starting library. An alternating pattern of negative round followed by a positive round of selections was then followed. In the negative rounds the sequences that bind TO1B in the absence of theophylline were depleted. The following positive round enriched for sequences that bind TO1B in the presence of theophylline. However, the presence of theophylline does not make it crucial to the binding of TO1B. The coupling of these two types of rounds minimizes the total number of selection rounds need to find the allosteric switches.

Results and Discussion

If coast is a concern, costs may be kept to a minimum by barcoding and mixing sets of selection. Here, two sets of selection experiments were barcoded and mixed in the final sequencing pool. Each pool of sequences had a unique sequence barcode added to FLA sequence for subsequent identification. Phased inserts were attached to the barcoded sequences to improve the efficiency of Illumina sequencing run. After sequencing, data was trimmed using custom python scripts and only used sequences that had the exact match to the truncated theophylline aptamer sequence. Pools were then separated out by barcode which identified the starting pool the sequence belonged to. Unique sequences in each pool were identified, counted, and relative abundance of each sequence was calculated. To calculate the relative abundance, the total counts of each unique sequence was assessed and divided those by the total pool count. We sequenced 5 RNA pools (R1-R5) in total and each pool contained the total 65,563 unique sequences at varying abundances.

The sequenced RNA pools were part of two separate experiments. In the first experiment, a pool of RNA (R5) that had most recently been through a negative selection was selected. A positive enrichment round was then performed and prepared the eluate pool for sequencing as stated above. Separately, R5 RNA was remade (R5a) and split the RNA pool into two separate equal molar pools (R6a). We performed a negative selection on one pool (R6a−) and a positive round on the other (R6a+). We then prepared the flow through from each pool for sequencing as described above.

Figure 7A:
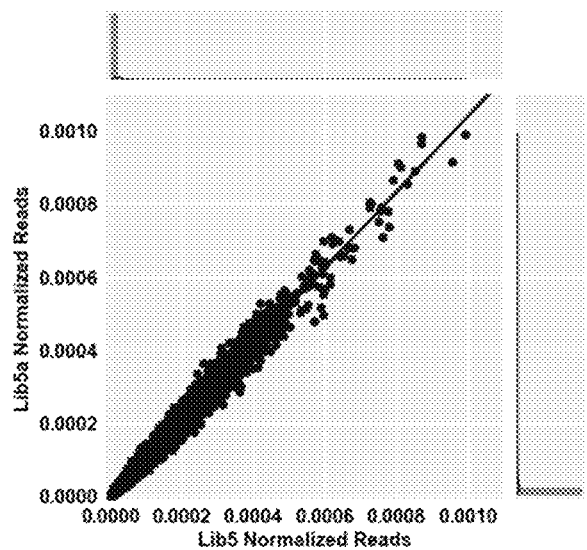
FIG. 7A is a graphical representation of the plots of sequences and their normalized reads for the two starting libraries (R5 and R5a) compared against each other.

The first analysis of the pool was to compare pools R5 and R5a to see if there were any significant differences between each pool. There was a correlation between the counts of each unique sequence between the two starting pools with an $R^2$ value of 0.989 (FIG. 7A). Normalized reads of R5 and R6 were then compared (FIG. 7B) and sequences were selected that exhibited an increase in count number from R5 to R6 as wells as sequences that had high R6:R5 ratios. It should be noted that there were no common sequences between the top twenty candidates in any of the analysis.

The second experimental analyzed the difference in enrichment between two experimental groups. Instead of calculating the fold difference between the two pools, the change in fold difference between the two experimental rounds was calculated (R6a+ and R6a−). The fold difference for R5a:R6a− and R5a:R6a+ was determined and then calculated the change in those ratios. We selected the sequences that exhibited depletion in the R6a+ pool and enrichment in the R6a− pool. Sequences that are bound to TO1B in the presence of theophylline will be depleted from the flow through due to the immobilization of the sequence to the TO1B on the beads in R6a+. The abundance of sequences in the flow through in R6a− was measured, as the sequences that are bound to TO1B in the absence of theophylline are removed from the flow through leaving sequences that require theophylline to bind TO1B.

Figure 8A:
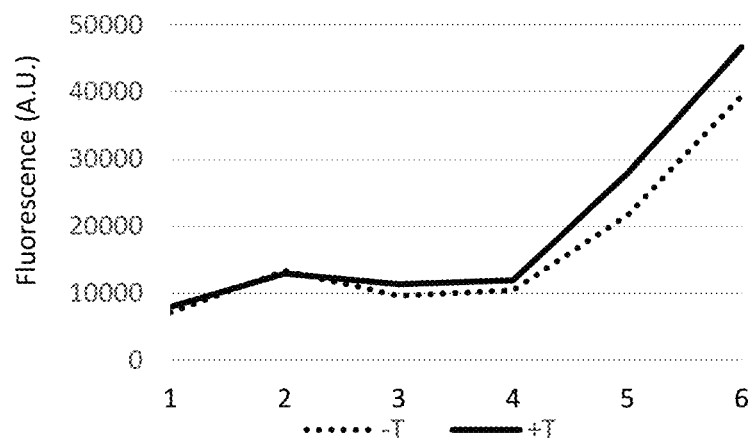
FIG. 8A is a graphical representation of the difference of fluorescence between RNA samples with theophylline (solid line) and without theophylline (dashed line) after every round of selection.
Figure 8B:
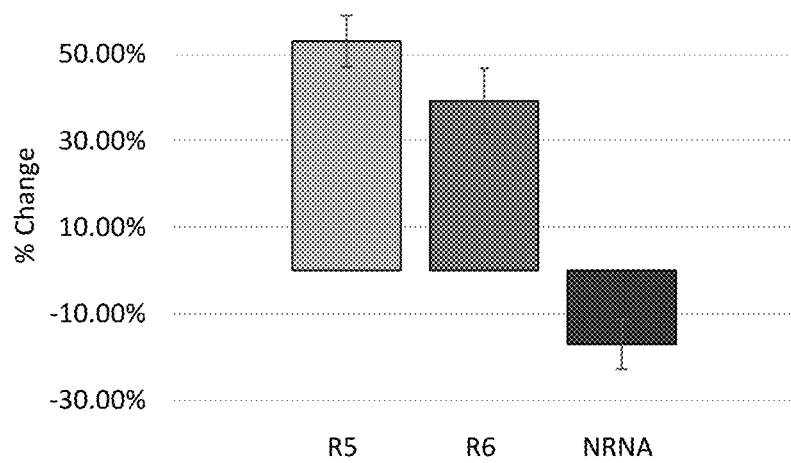
FIG. 8B is a graphical representation of the average change in fluorescence of samples R5 and R6 after the addition of theophylline.
Figure 8C:
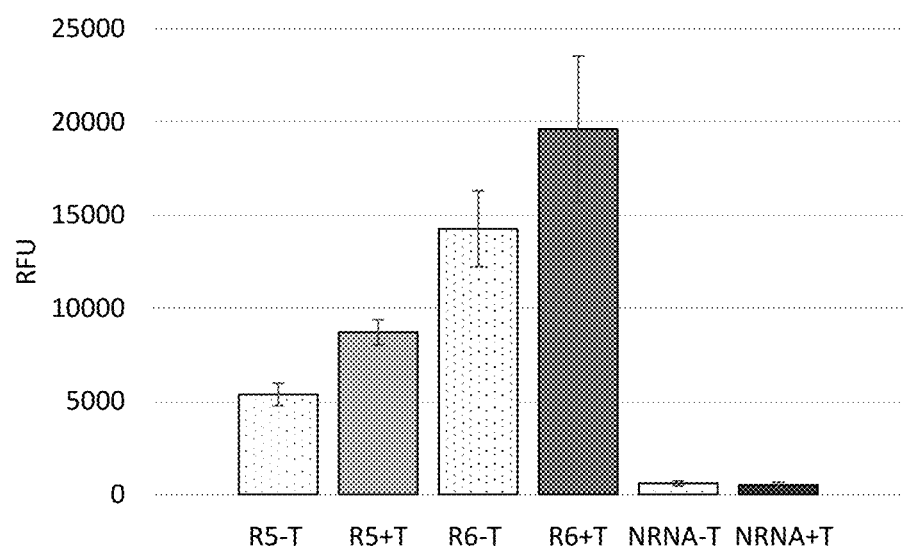
FIG. 8C is a graphical representation of the total brightness of fluorescence after the addition of theophylline for R % and R6 to confirmation verification.

Allosteric fluorescence was tested for each round of selection (FIG. 8A). In rounds 1-4, very little fluorescence enhancement when theophylline is added to the RNA pool was observed. In rounds 5 and 6 fluorescent enhancement was observed, as well as, an increase in overall fluorescent levels. On average there was a 53% (±5.9%) increase in fluorescence in R5 and a 39% (±7.5%) in R6 (FIG. 8B). There is an apparent decrease in fluorescence enhancement from R5 to R6 which is accompanied by an increase in total brightness (FIG. 8C).

Figure 7B:
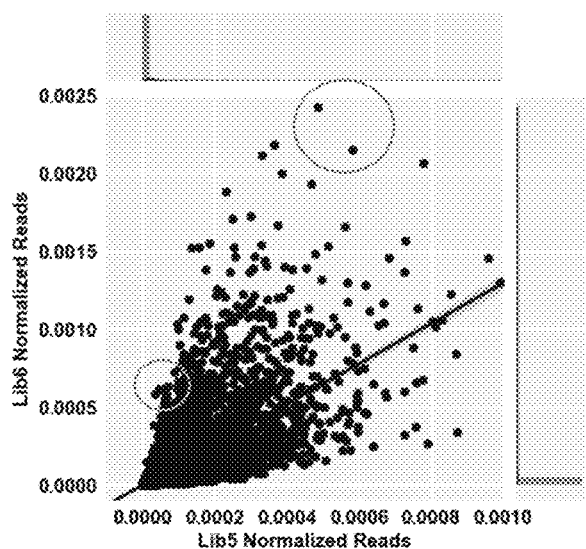
FIG. 7B is a graphical representation of the normalized reads for pools R6 and R5 compared against each other. Selected sequences that exhibited high enrichment ratios (lower circle) or high-count enrichment (top circle) and are predicted to exhibit allosteric fluorescence.
Figure 7C:
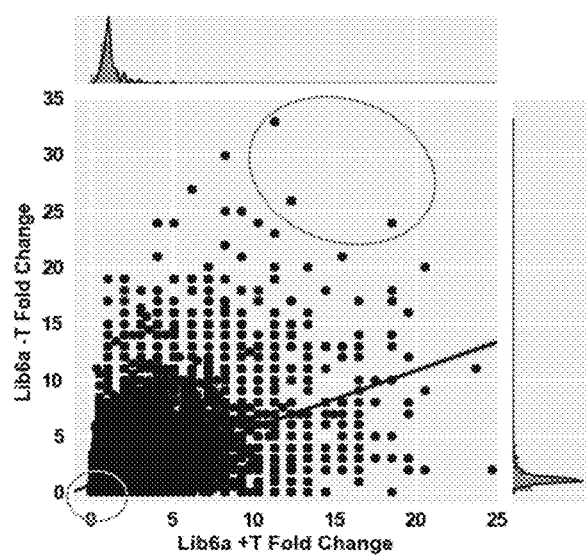
FIG. 7C is a graphical representation of the fold change of R6a+ and R6a− after being normalized to R5a pool. Selected sequences that are predicted to dim (anti) in the presence of theophylline (lower circle). Sequences that are predicted to exhibit allosteric fluorescence with theophylline (top circle).
Figure 8D:
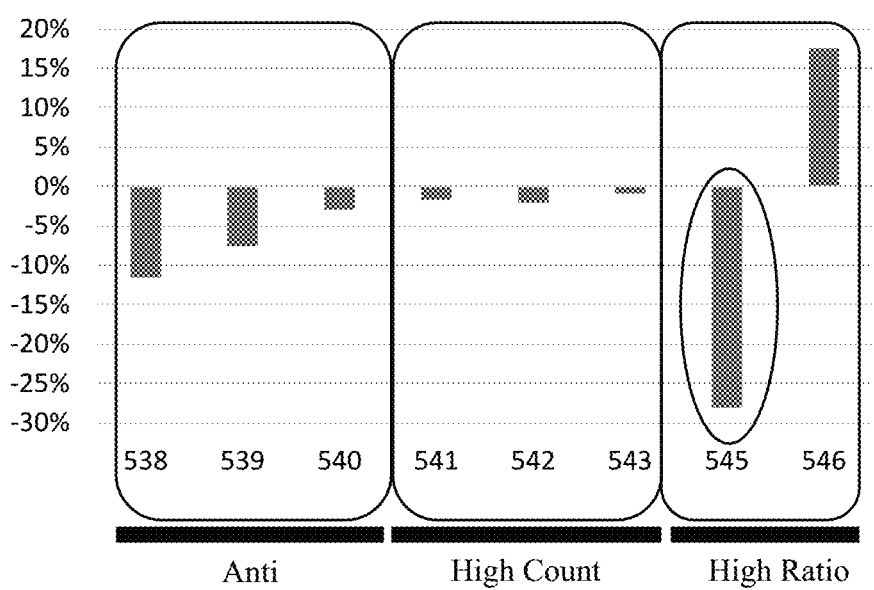
FIG. 8D is a graphical representation of the individual sequences with their change in fluorescence after the addition of theophylline grouped by sorting algorithm.

Single RNA sequences were screened individually for allosteric effects. Four groups of sequences were selected based on different criteria and the fluorescence enhancement of individual sequences was tested (FIGS. 7B and 7C, circles). Surprisingly, it was found that the fluorescence for MTS variant 545 decreased (FIG. 8D, circle). Variant 545 was predicted to be a good variant due to it having the largest enrichment ratio (data not shown). Previously, it has been shown that TO1B fluorescence brightness is generally correlated with $K_d$. However, surprisingly it was found that brightness of the TO1B does not correlate 100% with $K_d$. There have been several variants of reselected Mango, as well as our own 2S i-iv ii-i that have higher a higher $K_d$ as well as being brighter. Without being bound to a particular theory, the presence of theophylline is disrupting the binding pocket of the TO1B enough to destabilize the TO1B without disrupting the ability of the RNA strand to be immobilized by the TO1B molecule during the selections. Both 545 and 546 were in the "B" configuration and of the predicted switches isolated by our algorithm, library "B" was more than half of the reads followed by "C" and then "A". This suggests that the dim starting state of the MTS14B configuration may be the best starting position when considering design of allosteric fluorescent biosensors. There, it may be surprisingly easier to stabilize a dye than it is to enhance fluorescence through an allosteric mechanism.

Figure 9A:
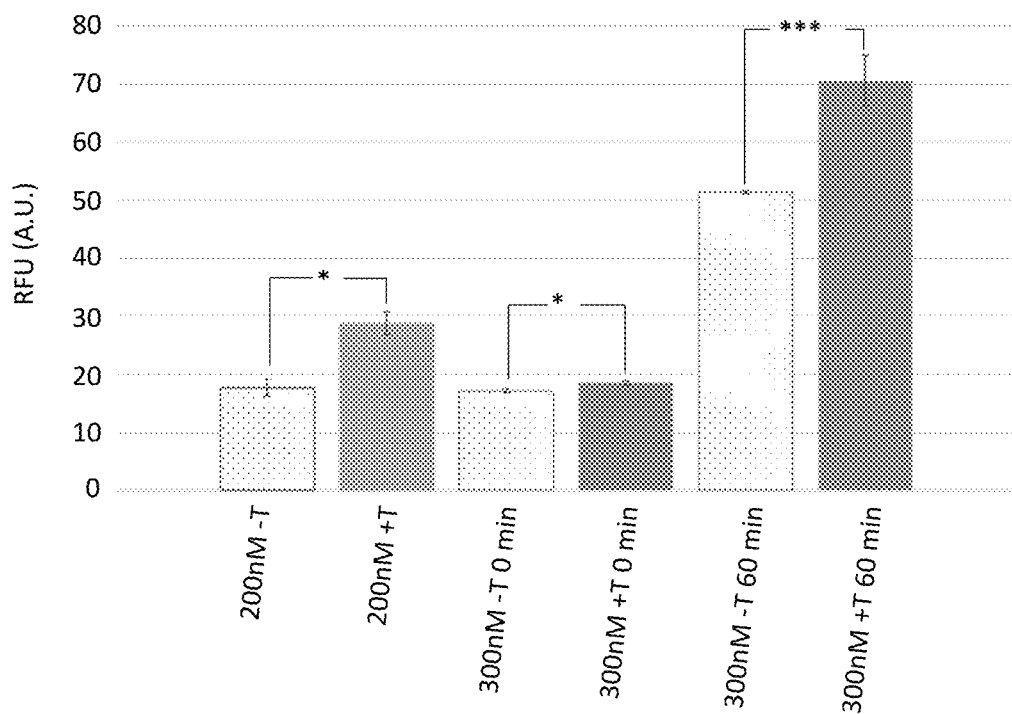
FIG. 9A is a graphical representation of the effects of theophylline saturation and time on the allosteric fluorescence of biosensor exemplar MTS546 showing the measured relative fluorescence of MTS546 at 200 nM RNA and 300 nM after incubation. Fluorescence measurements at time points of 0 minutes and 60 minutes for the same pool of RNA.

MTS546 exhibited allosteric fluorescence when saturated with theophylline. The best candidate over a range of theophylline at different RNA concentrations was tested. It was observed that there was significant allosteric fluorescence at multiple RNA concentrations. These results demonstrate that the biosensor has a greater fluorescent enhancement after the designed incubation time period with a p-value of <0.001 (FIG. 9A). The time-dependent fluorescence increase is since of all of the selection incubation times were greater than 30 minutes. It is not surprising that the biosensor requires an incubation time greater than 30 minutes. The concentrations of TO1B were held in excess of at least 5× for the fluorescence tests. This was done to ensure that each RNA molecule had an opportunity to bind a dye molecule. Unsurprisingly, the total brightness of the reactions increased with the increase in RNA concentration.

Figure 9B:
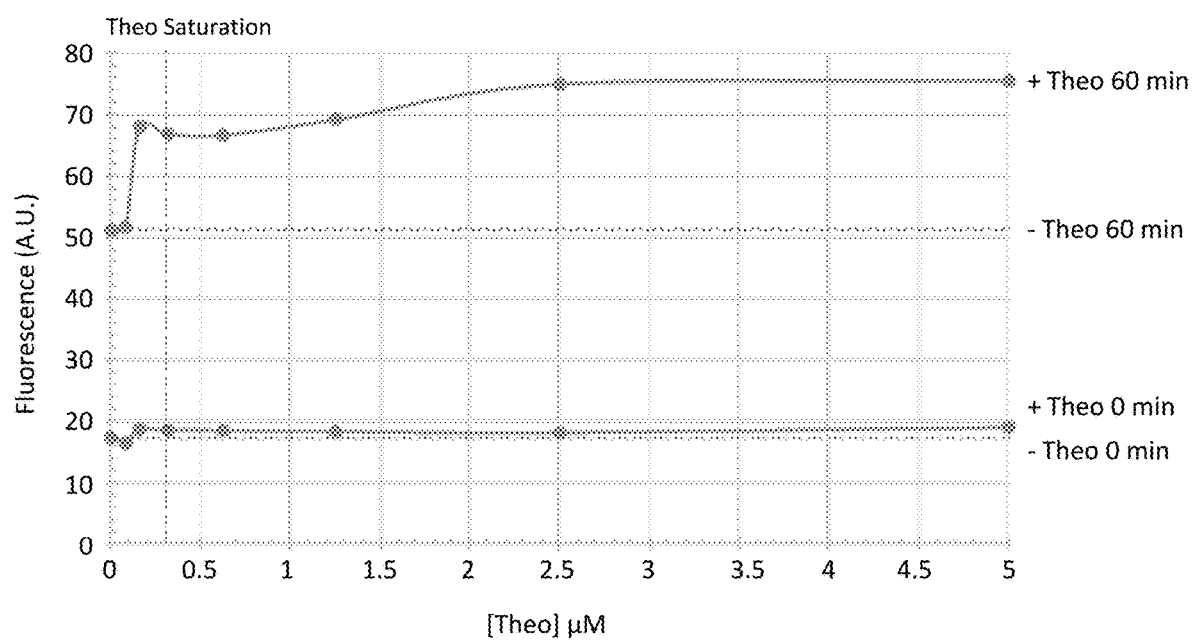
FIG. 9B is a graphical representation of the fluorescent saturation curves at different time points with theophylline (solid lines) and without theophylline (dashed lines). Theophylline saturation (vertical dashed line) where the concentration of theophylline equals the RNA concentration.

Statistical analysis showed that there is significant fluorescence enhancement when Theophylline is introduced to sample matrix. While it was seen that allosteric fluorescence in saturation, the dose-response is not quite clean enough to use to quantitate analyte in the sample (FIG. 9B). However, there is enough of a trend early in the fluorescent curve that suggests that this platform can be optimized for dose-response analysis. It is also anticipated that the fluorescent data will demonstrate linearity which is an important characteristic for in vitro diagnostics. While it remains to be seen if bead-based selection rounds can be designed for fluorescent enhancement, it is expected that technology exists to select for sequences that exhibit allosteric fluorescent.

Conclusion

Here it has been demonstrated that the plug and play can produce a biosensor for a small molecule and needs little user intervention beyond a single incubation. This work flow requires no washing and is congruent with many rapid screen in vitro diagnostics. The MTS546 construct demonstrates significant fluorescence enhancement before and after incubation. While it demonstrates allosteric fluorescence in saturation, it is not yet suitable for qualitative measurements below saturation, however, it is anticipated that this is possible. This design utilized 6 alternating negative-positive rounds of selection, which is nearly half of what was used during Mango I's initial selection rounds. This decrease in selection rounds is likely due to the relatively small N8 library size. Therefore, this disclosure teaches that using the design principals and procedural protocols described herein can be used to create new and novel biosensors that can detect a wide variety of effector molecules.

Example 3

RNA Components:
RNA theophylline with randomized 4 bp region (34 nts)

(SEQ ID NO: 13)
5' NNNNGAUACCAGCCGAAAGGCCCUUGGAGCNNNN

Five Prime Handle (Fh)

(SEQ ID NO: 14)
5' GGUCUAACCCUCAA

Three Prime Handle (Th)

(SEQ ID NO: 15)
5' AAAUAGACAGCCGAAGCC

DMS 14 A (SEQ ID NO: 3)
5' GGAUCGCGGAAGGGAGUACGUGCGAAAGCACGUACGAAGGUGCGGAG

AGGAGACGCGAUCC

DMS 14B (SEQ ID NO: 4)
5' GGAUCGCGGAAGGGACGGUGAGUACGUGCGAAAGCACGUACGAAGGA

GAGGAGACGCGAUCC

DMS 14 C (SEQ ID NO: 5)
5' GGAUCGCGGAAGGGACGGUGCGGAGAGUACGUGCGAAAGCACGUACG

AAGGAGACGCGAUCC

RNA Domain Substitutions:
14A-Fh-Man8-N8Theo-Th (106 nts) ε = 1.0426 uM$^{-1}$ cm$^{-1}$ (SEQ ID NO: 16)
5' GGUCUAACCCUCAAGGAUCGCGGAAGGGANNNNGAUACCAGCCGAAA

GGCCCUUGGAGCNNNNGAAGGUGCGGAGAGGAGACGCGAUCCAAAUAGAC

AGCCGAAGC

14B-Fh-Man8-N8Theo-Th (107 nts) ε = 1.0560 uM$^{-1}$ cm$^{-1}$ (SEQ ID NO: 17)
5' GGUCUAACCCUCAAGGAUCGCGGAAGGGACGGUGANNNNGAUACCAG

CCGAAAGGCCCUUGGAGCNNNNGAAGGAGAGGAGACGCGAUCCAAAUAGA

CAGCCGAAGC

14C-Fh-Man8-N8Theo-Th (107 nts) ε = 1.0494 uM$^{-1}$ cm$^{-1}$ (SEQ ID NO: 18)
5' GGUCUAACCCUCAAGGAUCGCGGAAGGGACGGUGCGGAGANNNNGAU

ACCAGCCGAAAGGCCCUUGGAGCNNNNGAAGGAGACGCGAUCCAAAUAGA

CAGCCGAAGC ssDNA (RC RNA) with T7 Promoter:
14A-Fh-Man8-N8Theo-Th (123 nts) ε = 1.114 uM$^{-1}$ cm$^{-1}$ (SEQ ID NO: 19)
5' GCTTCGGCTGTCTATTTGGATCGCGTCTCCTCTCCGCACCTTCNNNN

GCTCCAAGGGCCTTTCGGCTGGTATCNNNNTCCCTTCCGCGATCCTTGAG

GGTTAGACCTATAGTGAGTCGTATTA

14B-Fh-Man8-N8Theo-Th (124 nts) ε = 1.124 uM$^{-1}$ cm$^{-1}$ (SEQ ID NO: 20)
5' GCTTCGGCTGTCTATTTGGATCGCGTCTCCTCTCCTTCNNNNGCTCC

AAGGGCCTTTCGGCTGGTATCNNNNTCACCGTCCCTTCCGCGATCCTTGA

GGGTTAGACCTATAGTGAGTCGTATTA

14C-Fh-Man8-N8Theo-Th (124 nts) ε = 1.125 uM$^{-1}$ cm$^{-1}$ (SEQ ID NO: 21)
5' GCTTCGGCTGTCTATTTGGATCGCGTCTCCTTCNNNNGCTCCAAGGG

CCTTTCGGCTGGTATCNNNNTCTCCGCACCGTCCCTTCCGCGATCCTTGA

GGGTTAGACCTATAGTGAGTCGTATTA

Primers: Ta = 53° C.
R-Primer (H358)

(SEQ ID NO: 22)
5' GGCTTCGGCTGTCTATTTGGATC

F-Primer (H359)

(SEQ ID NO: 23)
5' TAATACGACTCACTATAGGTCTAACCCTCAAGGATCG

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

---

What is claimed is:

1. An oligonucleotide biosensor for detecting a target ligand in a sample, comprising:
   a reporter domain having a fluorophore binding region and an open stem region;
   one or more linker domains attached between the reporter domain and a target domain; and
   one or more target domains attached to a linker domain or another target domain, wherein the reporter domain is represented by the RNA sequence: 5'-GG@($T_1$/WGW)GG(#$_1$H/WG)WGGN@(#$_2$/-)G($T_2$/H)GNH(AN@$T_3$/G)-3' (SEQ ID NO: 1)
   where:
   - represents no nucleotide (gap);
   K represents U or G;
   S represents C or G,
   R represents A or G;
   W represents A or U;
   H represents A, C, or U;
   N represents A, C, G, or U; and
   @ represents N or no nucleotide;
   wherein/between the brackets ( ) represents an alternative; and wherein $T_1$ represents any nucleotide, $T_2$ and $T_3$ being defined as follows:
      when $T_1$ is A, $T_2$ can be either A, G or U; and
         when $T_1$ is A and $T_2$ is A, then $T_3$ is U;
         when $T_1$ is A and $T_2$ is G, then $T_3$ is U; and
         when $T_1$ is A and $T_2$ is U, then $T_3$ is A or U; or
      when $T_1$ is C, $T_2$ can be either G or U; and
         when $T_1$ is C and $T_2$ is G, then $T_3$ is C or G; and
         when $T_1$ is C and $T_2$ is U, then $T_3$ is G; or
      when $T_1$ is G, $T_2$ can be either G or C, and $T_3$ is C; or
      when $T_1$ is U, $T_2$ can be either A or C; and
         when $T_1$ is U and $T_2$ is A, then $T_3$ is A or U; and
         when $T_1$ is U and $T_2$ is C, then $T_3$ is A;
   wherein #$_1$ and #$_2$ represents any nucleotide pair such that:
      when #$_1$ is A, then #$_2$ represents A, C, G, or U; or
      when #$_1$ is C, then #$_2$ is C; or
      when #$_1$ is G, then #$_2$ is G; or
      when #$_1$ is U, then #$_2$ represents A, G, or U,
   wherein #$_1$ and #$_2$ represents any nucleotide pair such that:
      when #$_1$ is A, then #$_2$ represents A, C, G, or U; or
      when #$_1$ is C, then #$_2$ is C; or
      when #$_1$ is G, then #$_2$ is G; or
      when #$_1$ is U, then #$_2$ represents A, G, or U,
   wherein the aptamer adopts a determined tridimensional conformation which is a fluorophore binding conformation, said aptamer when it adopts the fluorophore binding conformation being liable to interact with a fluorophore; wherein the aptamer further comprises, contiguous with the active core sequence, a 5' leader sequence attached, or operably linked to (by covalent bound, i.e. phosphodiester bound), to the 5' terminus of the active core and a 3' tail sequence attached, or operably linked to (by covalent bridge mentioned below), to the 3' terminus of the active core, wherein the 5' leader sequence and the 3' tail sequence together mediate the juxtaposition of the 5' terminus of the active core and the 3' terminus of the active core when the aptamer is the fluorophore binding conformation.

2. The biosensor of claim 1, wherein the reporter domain is a Mango core.

3. The biosensor of claim 2, wherein the Mango core is Mango I.

4. The biosensor of claim 1, wherein the reporter domain binds to a molecule defined by Formula I or II.

5. The biosensor of claim 1, wherein the reporter domain has a binding affinity of at least about 400 nM.

6. The biosensor of claim 1, wherein the reporter domain increases the brightness of a fluorophore by at least 7,000 M/cm.

7. The biosensor of claim 1, wherein the $K_d$ of the reporter domain for the fluorophore is at least about 2.0 µM.

8. The biosensor of claim 1, wherein the linker domain partially disrupts the target domain.

9. The biosensor of claim 1, wherein the linker domain is attached to the reporter domain opposite of the reporter domain open stem.

10. The biosensor of claim 1, wherein the linker domain is about 40 nucleotides or less.

11. The biosensor of claim 1, wherein the linker domain is between about 2 and about 14 nucleotides.

12. The biosensor of claim 1, wherein the linker domain is lacks the tetraloop-like motif GAAA.

13. The biosensor of claim 1, wherein the target domain has an affinity for a target ligand such that $K_d<500$ nM.

14. The biosensor of claim 1, wherein the target domain is a closed stem.

15. The biosensor of claim 1, wherein the target domain is an open stem.

16. The biosensor of claim 1, wherein the target domain binds to one or more target ligands selected from proteins, nucleic acids (RNA or DNA), lipids, oligosaccharides, carbohydrates, small molecules, hormones, cytokines, chemokines, cell signaling molecules, metabolites, organic molecules, and metal ions.

17. The biosensor of claim 1, further comprising handles, barcodes or promoters.

18. The biosensor of claim 1, wherein the biosensor is a continuous oligonucleotide.

19. The biosensor of claim 1, wherein the biosensor comprises of two or more oligonucleotides.

20. An expression vector comprising the biosensor of claim 1.

21. A method of enriching a pool of randomly generated biosensors for a target ligand, comprising:
obtaining a pool of randomly generated bio sensors of claim 1; and
alternating between negative and positive selection.

22. The method of claim 21, further comprising:
sequencing the pools following each round of selection;
comparing the changes in counts or fold changes between the rounds.

23. The method of claim 22, further comprising:
splitting the pool into two or more equal molar pools;
performing negative selection on a first sub-pool and negative selection on a second sub-pool;
sequencing the pools; and
calculating the fold change differences when compared with the initial pool.

24. The method of claim 23, wherein there are 10 or fewer rounds of total selection.

25. A method of detecting a target ligand in a sample using a biosensor of claim 1, comprising:
introducing the bio sensor of claim 1 and a fluorophore compatible with the reporter domain of the biosensor into the sample;
incubating the same with the biosensor and fluorophore; and
measuring the change in fluorescence of the fluorophore.

26. The method of claim 25, further comprising introducing a reference dye into the sample.

27. The method of claim 25, wherein the change in fluorescence increases in the presence of the target ligand.

28. The method of claim 25, wherein the change in fluorescence decreases in the presence of the target ligand.

29. A method of detecting a target ligand in a cell using an expression vector of claim 20, comprising:
introducing the expression vector of claim 22 into the cell;
introducing a fluorophore compatible with the reporter domain of the biosensor expressed by the expression vector into the cell;
incubating the same with the biosensor and fluorophore; and
measuring the change in fluorescence of the fluorophore.

30. The method of claim 29, further comprising introducing a reference dye into the cell.

31. A kit comprising of:
an oligonucleotide biosensor of claim 1;
a fluorophore compatible with the reporter domain of the oligonucleotide;
buffer; and
instructions.

32. The kit of claim 31, further comprising a reference dye.

* * * * *

UNITED STATES PATENT AND TRADEMARK OFFICE
CERTIFICATE OF CORRECTION

PATENT NO. : 11,976,382 B2
APPLICATION NO. : 16/949217
DATED : May 7, 2024
INVENTOR(S) : Steven Burden, Eric Hayden and Nicholas Shults Page 1 of 1

It is certified that error appears in the above-identified patent and that said Letters Patent is hereby corrected as shown below:

In the Claims

Column 59, Claim 21, Line 22:
INSERT --of claim 1-- after "biosensors"

Column 59, Claim 21, Line 23:
DELETE "bio sensors" after "generated"
INSERT --biosensors-- after "generated"

Column 60, Claim 25, Line 5:
DELETE "bio sensor" after "the"
INSERT --biosensor-- after "the"

Signed and Sealed this
Sixth Day of August, 2024

Katherine Kelly Vidal
*Director of the United States Patent and Trademark Office*